US012324833B2

(12) United States Patent
Li et al.

(10) Patent No.: US 12,324,833 B2
(45) Date of Patent: Jun. 10, 2025

(54) RECOMBINANT SEVERE RESPIRATORY SYNDROME CORONAVIRUS 2 Rbd TRIMER PROTEIN VACCINE CAPABLE OF GENERATING BROAD-SPECTRUM CROSS NEUTRALIZATION ACTIVITY, AND PREPARATION METHOD AND USE THEREOF

(71) Applicant: NATIONAL VACCINE AND SERUM INSTITUTE(NVSI), Beijing (CN)

(72) Inventors: Qiming Li, Beijing (CN); Yu Liang, Beijing (CN); Jing Zhang, Beijing (CN); Jiguo Su, Beijing (CN); Zibo Han, Beijing (CN); Shuai Shao, Beijing (CN); Yanan Hou, Beijing (CN); Hao Zhang, Beijing (CN); Shi Chen, Beijing (CN); Yuqin Jin, Beijing (CN); Xuefeng Zhang, Beijing (CN); Lifang Du, Beijing (CN); JunWei Hou, Beijing (CN); Zhijing Ma, Beijing (CN); Zehua Lei, Beijing (CN); Fan Zheng, Beijing (CN); Fang Tang, Beijing (CN); Zhaoming Liu, Beijing (CN); Ning Liu, Beijing (CN)

( * ) Notice: Subject to any disclaimer, the term of this patent is extended or adjusted under 35 U.S.C. 154(b) by 0 days.

(21) Appl. No.: 18/277,087

(22) PCT Filed: Sep. 24, 2021

(86) PCT No.: PCT/CN2021/120447

§ 371 (c)(1),
(2) Date: Aug. 14, 2023

(87) PCT Pub. No.: WO2022/262142

PCT Pub. Date: Dec. 22, 2022

(65) Prior Publication Data

US 2024/0325520 A1 Oct. 3, 2024

(30) Foreign Application Priority Data

Jun. 18, 2021 (CN) ........................ 202110676901.2

(51) Int. Cl.

| | |
|---|---|
| ***A61K 39/215*** | (2006.01) |
| ***A61K 39/00*** | (2006.01) |
| ***A61P 31/14*** | (2006.01) |
| ***C07K 14/005*** | (2006.01) |
| ***C12N 7/00*** | (2006.01) |

(52) U.S. Cl.

CPC ............ *A61K 39/215* (2013.01); *A61P 31/14* (2018.01); *C07K 14/005* (2013.01); *C12N 7/00* (2013.01); *A61K 2039/55505* (2013.01); *A61K 2039/575* (2013.01); *A61K 2039/70* (2013.01); *C12N 2770/20022* (2013.01); *C12N 2770/20034* (2013.01)

(58) Field of Classification Search

CPC ........ A61K 39/215; A61K 2039/55505; A61K 2039/575; A61K 2039/70; A61P 31/14; C07K 14/005; C12N 7/00; C12N 2770/20022; C12N 2770/20034

See application file for complete search history.

(56) References Cited

U.S. PATENT DOCUMENTS

| | | | | |
|---|---|---|---|---|
| 10,906,944 | B2 * | 2/2021 | He | C12N 7/00 |
| 11,845,777 | B2 * | 12/2023 | He | A61K 39/215 |
| 2024/0140993 | A1 * | 5/2024 | He | A61P 31/14 |

FOREIGN PATENT DOCUMENTS

| | | | | |
|---|---|---|---|---|
| CN | 112048005 A | * 12/2020 | | A61K 39/12 |
| CN | 112679587 A | * 4/2021 | | |
| CN | 112760341 A | * 5/2021 | | A61K 39/12 |
| CN | 112794884 A | * 5/2021 | | C07K 14/005 |
| WO | WO-2022032660 A1 | * 2/2022 | | |
| WO | WO-2022206222 A1 | * 10/2022 | | A61K 39/12 |
| WO | WO-2022207645 A1 | * 10/2022 | | A61K 39/12 |
| WO | WO-2023025287 A1 | * 3/2023 | | |

OTHER PUBLICATIONS

Wang, Z. et al. (2021). mRNA vaccine-elicited antibodies to SARS-CoV-2 and circulating variants. Nature, 592(7855), 616-622. (Year: 2021).*

Tong and Dong. 2020. CN 112048005 A. Machine Translation. (Year: 2020).*

Gao et al. 2021. CN 112794884 A. Machine Translation (Year: 2021).*

Zhang et al. 2021. CN 112679587 A. Machine Translation. (Year: 2021).*

Gao et al. 2021. CN 112760341 A. Machine Translation. (Year: 2021).*

Hu et al. 2023. WO 2023025287 A1. Machine Translation. (Year: 2023).*

Dai, L. et al. (2020). A Universal Design of Betacoronavirus Vaccines against COVID-19, MERS, and SARS. Cell, 182(3), 722-733. e11. (Year: 2020).*

Fang et al. 2022. WO 2022/032660 A1. Machine translation. (Year: 2022).*

Li et al. 2022. WO 2022/206222 A1. Machine translation. (Year: 2022).*

(Continued)

*Primary Examiner* — Janet L Andres
*Assistant Examiner* — Carey Alexander Stuart

(57) ABSTRACT

The present invention provides a recombinant RBD trimer protein capable of simultaneously generating cross neutralization activity for various severe acute respiratory syndrome coronavirus 2 (SARS-COV-2) epidemic strains. The RBD trimer protein is taken as an antigen and supplemented with an adjuvant to immunize an organism, so that a high-titer neutralizing antibody aiming at various SARS-COV-2 epidemic strains can be generated at the same time, and the antibody has a certain broad-spectrum property and can be used for treating and/or preventing SARS-COV-2 infection and/or coronavirus disease 2019.

20 Claims, 12 Drawing Sheets

Specification includes a Sequence Listing.

(56) References Cited

OTHER PUBLICATIONS

Zhang et al. Broad protective RBD heterotrimer vaccines neutralize SARS-CoV-2 including Omicron subvariants XBB/BQ.1.1/BF.7, PLOS Pathogens, published on Sep. 18, 2023, available from https://doi.org/10.1371/journal.ppat.1011659.

* cited by examiner

A

B

RECOMBINANT SEVERE RESPIRATORY SYNDROME CORONAVIRUS 2 Rbd TRIMER PROTEIN VACCINE CAPABLE OF GENERATING BROAD-SPECTRUM CROSS NEUTRALIZATION ACTIVITY, AND PREPARATION METHOD AND USE THEREOF

CROSS-REFERENCE

This application claims the priority of a Chinese patent application entitled "RECOMBINANT SEVERE ACUTE RESPIRATORY SYNDROME CORONAVIRUS 2 RBD TRIMER PROTEIN VACCINE CAPABLE OF GENERATING BROAD-SPECTRUM CROSS NEUTRALIZATION ACTIVITY, AND PREPARATION METHOD AND USE THEREOF" submitted to the China Patent Office on Jun. 18, 2021, with application No. 202110676901.2, and the entire content of which is incorporated in this application by reference.

INCORPORATION BY REFERENCE

The present invention contains an ASCII plain text file for a sequence listing titled "KC39990_PCT21002--000001_sequencelisting_amended-JH.txt" created 2024 May 20 having a size of 67 KB, which is now incorporated by reference to the present invention.

TECHNICAL FIELD

The present invention relates to the field of biological drugs, and in particular to a recombinant SARS-CoV-2 RBD trimer protein vaccine capable of generating broad-spectrum cross neutralization activity, and a preparation method and use thereof.

BACKGROUND

Severe acute respiratory syndrome coronavirus 2 (SARS-CoV-2) belongs to a single-stranded positive strand RNA virus, SARS-like virus species, sarbecovirus subgenus, beta-coronavirus, positive coronavirus, coronaviridae, nidovirales, with a cyst membrane. The full length of genome is about 29.9 kb. Most of the genome encodes non-structural proteins and participates in virus replication and translation functions; and a few sequences encode structural proteins, such as a spike protein (S protein), a membrane protein (M protein), a cyst membrane protein (E protein) and a nucleo protein (N protein). In addition, there are several accessory proteins: 3a, 3b, p6, 7a, 7b, 8b, 9b and or f14, and these proteins participate in viral assembly. S, M and E proteins constitute a virus cyst membrane, which is a main surface antigen of the virus causing immune response. The S protein is a transmembrane glycoprotein, has a molecular weight about 150 kDa, and forms a prominent homotrimer on the surface of the virus. The S protein consists of two functional subunits, and is cleaved at a boundary (an S1/S2 cleavage site) between the S1 subunit and the S2 subunit; and the two subunits keep non-covalent binding in conformation before fusion. The S2 subunit is composed of a plurality of structural domains, and has a main function of mediating the fusion between a virus and a host cell. The distal S1 subunit is structurally divided into four different structural domains: a N-terminal structural domain (NTD), a receptor binding structural domain (RBD), a C-terminal structural domain 1 (CTD1) and a C-terminal structural domain 2 (CTD2), where RBD is mainly responsible for binding with a receptor angiotensin converting enzyme 2 (ACE2) on the surface of the host cell, so that the virus is mediated to infect the host cell; therefore, the S protein and RBD are the main targets of the research and development of genetic engineering vaccine at present.

Up to now, there are totally eight vaccines approved for listing in the world, namely BNT162b2 and mRNA-1273 approved by the United States for emergency use authorization (EUA), AZD1222 approved by the United Kingdom for EUA, three types of COVID-19 inactivated vaccines from China National Biotec Group (Beijing company and Wuhan company) and Beijing Sinovac Biotech Ltd., CanSinoBIO adenovirus vector vaccines and Zhifei Biological recombinant protein vaccines, and "satellite V" approved by Russia for listing. In addition, there are dozens of vaccines in different stages of clinical research. No matter which technical route these listed vaccines come from, different contributes are made to epidemic prevention and control. However, due to the evolution of SARS-CoV-2, various mutations occur continuously, so that the protective effect of existing vaccines is affected to varying degrees.

SARS-CoV-2 belongs to an RNA virus, which is prone to mutation. More than 30,000 SARS-CoV-2 mutant strains have been reported in the world, mainly including: an alpha (B.1.1.7) mutant strain, a beta (B.1.351) mutant strain, a gamma (P1) mutant strain, an epsilon (B.1.429) mutant strain, a delta (B.1.617.2) mutant strain, and a kappa (B.1.617.1) mutant strain. The mutation sites of these mutant strains are mainly present in the amino acid sequences of the S protein, in particular an RBD region. Therefore, mutation may improve the affinity between the virus and an ACE2 receptor and attenuating neutralizing antibody effect, so that the virulence and infectivity of the virus are enhanced, virus escape is accelerated, and the protective effect of the vaccines is reduced. Therefore, it is urgent to develop a broad-spectrum vaccine against various SARS-CoV-2 epidemic strains.

SUMMARY

For the technical defect of lacking a broad-spectrum severe acute respiratory syndrome coronavirus 2 (SARS-CoV-2) vaccine in the prior art, the present invention provides a single-component broad-spectrum RBD trimer protein vaccine capable of generating high cross neutralization activity for various SARS-CoV-2 epidemic strains.

The technical solution provided by the present invention is as follows:

a recombinant SARS-CoV-2 RBD trimer protein capable of generating broad-spectrum cross neutralization activity, where the trimer protein is composed of subunits of three SARS-CoV-2 RBD regions, and the amino acid sequences of the three SARS-CoV-2 RBD regions are the same or at least one of the three is different; and when the amino acid sequences of the three SARS-CoV-2 RBD regions are the same, the amino acid sequences are the amino acid sequences shown in SEQ ID NO.2 or SEQ ID NO.3, or sequences with more than 95% of homology with the amino acid sequences shown in SEQ ID NO.2 or SEQ ID NO.3.

According to the present invention, a brand-new fusion protein is designed by a computational biology method based on the structural feature of a SARS-CoV-2 RBD region. The protein includes three RBD structural domains, which can form a trimer form with stable antigen conformation without introducing any exogenous linking arm or other irrelevant components, thereby realizing RBD protein trimerization. After recombinant expression and purification of an RBD trimer protein by a genetic engineering technology, the protein and an adjuvant are mixed to prepare a vaccine. After immunization with a certain dosage and times, a protective neutralizing antibody for various SARS-CoV-2 epidemic strains can be generated for treating and/or preventing SARS-CoV-2 infection and/or coronavirus disease 2019 (COVID-19). The RBD region has a clear function and structure and is responsible for identifying an ACE2 receptor of a host cell, and the antibody generated for the RBD has a clear function and a specific target, thereby preventing from inducing an organism to produce antibody dependent enhancement (ADE).

The trimer protein in the present invention is composed of amino acid fragments of three SARS-CoV-2 RBD regions that are connected in an order from an N terminal to a C terminal.

In the present invention, a length of peptide chains of three RBD region subunits of the trimer protein may be a full length of the SARS-CoV-2 S protein RBD region. Preferably, in the embodiments of the present invention, the length of the peptide length of the SARS-CoV-2 RBD region is at least 50% to 99% of the full length of the RBD region sequence.

50% to 99% of the full length of the RBD region may be 50%, 60%, 70%, 80%, 90% or 99% of the full length of the RBD region, and at least includes one or more different amino acid residues.

More preferably, in one embodiment of the present invention, the amino acid sequences of the SARS-CoV-2 RBD region are the 319th to 537th amino acids of the S protein.

In the present invention, the amino acid sequences of the SARS-COV-2 RBD region may be from RBD structural domains of S protein of different SARS-COV-2 epidemic strains, for example, the prototype strain SARS-COV-2, Kappa (B.1.617) SARS-COV-2 carrying L452R and E484Q mutants, SARS-COV-2 carrying a D614G mutant, SARS-COV-2 carrying an L452R mutant. Alpha (B.1.1.7) SARS-COV-2 carrying a plurality of mutants N501Y, P681H and 69-70del, Beta (B.1.135) SARS-COV-2 carrying a plurality of mutants N501Y, K417N and E484K, and Gamma (P.1) SARS-COV-2 carrying NSO1Y, E484K and K417T mutants. The above sequences may be obtained through NCBI.

Preferably, in the embodiments of the present invention, the amino acid sequences of the SARS-CoV-2 RBD region are amino acid sequences shown in SEQ ID NO.1, SEQ ID NO.2 or SEQ ID NO.3, or sequences with more than 95% of homology with the amino acid sequences shown in SEQ ID NO.1, SEQ ID NO.2 or SEQ ID NO.3.

In the above embodiments, the trimer protein provided by the present invention may form a trimer form with stable antigen conformation without introducing any exogenous linking arm or other irrelevant components.

In the above embodiments, the amino acid sequences shown in SEQ ID NO.1, SEQ ID NO.2 or SEQ ID NO.3 may obtain new amino acid sequences by substituting, deleting or inserting one or more amino acid sequences. A new protein formed by the amino acid sequences has the same or basically the same immunological activity as the protein composed of the amino acid sequences shown in SEQ ID NO.1, SEQ ID NO.2 or SEQ ID NO.3. The new amino acid sequences may be considered to be included in the protection scope of the present invention.

Then, the sequences with more than 95% of homology with the amino acid sequences refer to amino acid sequences having 95%, 96%, 97%, 98% or 99% identity to the amino acid sequences of the recombinant SARS-CoV-2 RBD trimer protein or the fusion protein. Those skilled in the art can perform random or engineered point mutation on the amino acid sequences of the fusion protein in the specification, with the purpose of, for example, obtaining higher affinity and/or dissociation property and improving the expression performance. These sequences may have the same or basically the same immunological activity as the SARS-CoV-2 RBD trimer protein or the fusion protein, and these mutated amino acid sequences are all included in the protection scope of the present invention.

In the present invention, the three SARS-CoV-2 RBD regions with the same or at least one different amino acid sequence may be connected in any order from an N terminal to a C terminal. For example, in the embodiments of the present invention, the amino acid sequences of the protein formed by sequentially connecting SEQ ID NO.1, SEQ ID NO.2 and SEQ ID NO.3 is shown in SEQ ID NO.4; the amino acid sequences of the protein formed by sequentially connecting SEQ ID NO.1, SEQ ID NO.2 and SEQ ID NO.1 is shown in SEQ ID NO.5; the amino acid sequences of the protein formed by sequentially connecting SEQ ID NO.1. SEQ ID NO.2 and SEQ ID NO.2 is shown in SEQ ID NO.6; the amino acid sequences of the protein formed by sequentially connecting SEQ ID NO.2, SEQ ID NO.1 and SEQ ID NO.2 is shown in SEQ ID NO.7; and the amino acid sequences of the protein formed by sequentially connecting SEQ ID NO.2, SEQ ID NO.2 and SEQ ID NO.2 is shown in SEQ ID NO.8, or any other combination.

Preferably, in one embodiment of the present invention, the amino acid sequences of the trimer protein is amino acid sequences shown in SEQ ID NO.4, or sequences with more than 95% of homology with the amino acid sequences shown in SEQ ID NO.4.

Another aspect of the present invention provides a fusion protein. The fusion protein includes the recombinant SARS-CoV-2 RBD trimer protein.

Preferably, in the embodiments of the present invention, the fusion protein further includes one or more of signal peptides, tags or immune-enhancing peptides. The signal peptides may be more favorable for the expression of protein; and the tags may be, for example, flag tags, enhanced green fluorescence protein (eGFP), glutathione S-transferase (GST) and the like, and may be used for detection, purification, separation and the like. The above functional sequences may be used in any combination.

Another aspect of the present invention provides a nucleic acid molecule. The nucleic acid molecule includes a nucleotide sequence encoding the recombinant SARS-CoV-2 RBD trimer protein or encoding the fusion protein.

Preferably, in one embodiment of the present invention, the inventor optimizes a codon of the trimer protein, and the obtained nucleotide sequence is shown in SEQ ID NO.9 to SEQ ID NO.17 or sequences with more than 95% of homology with the amino acid sequences shown in SEQ ID NO.9 to SEQ ID NO.17.

The sequences with more than 95% of homology with the amino acid sequences refer to nucleotide sequences which are 95%, 96%, 97%, 98% or 99% the same as the nucleotide sequences.

For a method for preparing the nucleic acid molecule, the nucleic acid molecule may be prepared based on the above nucleotide sequences through known technologies such as chemical synthesis or PCR amplification. Generally, the codon of the amino acid encoding the above structural domain may be optimized to optimize the expression in a host cell. The information of the base sequence may be obtained by retrieving a database such as a known literature or NCBI.

Another aspect of the present invention provides a vector. The vector includes the nucleic acid molecule.

In the present invention, the vector may be a linear vector or a circular vector. The vector may be a non-viral vector such as plasmid, or a virus vector, or a vector using a transposon. The vector may include a promoter, a terminator or other regulatory sequences, and a drug resistance gene, a reporter gene or other marker sequence.

Preferably, in one embodiment of the present invention, the vector is an expression vector of the nucleic acid molecule in the present invention.

Another aspect of the present invention provides a host cell. The host cell includes the nucleic acid molecule or the vector.

Preferably, in the embodiments of the present invention, the host cell is *Escherichia coli*, a yeast cell, an insect cell or a mammalian cell.

Preferably, in one embodiment of the present invention, the host cell is a CHO cell.

Another aspect of the present invention provides a method for preparing the recombinant SARS-CoV-2 RBD trimer protein or the fusion protein, including the following steps:

step A): preparing the nucleic acid molecule, constructing an expression vector of the nucleic acid molecule, and transforming or transfecting the expression vector into the host cell;

step B): performing protein expression by using a product in step A); and step C): purifying an expression product obtained in step B) to obtain the recombinant SARS-CoV-2 RBD trimer protein or the fusion protein.

In step A), the nucleic acid molecule includes a nucleotide sequence encoding the recombinant SARS-CoV-2 RBD trimer protein or encoding the fusion protein.

Preferably, in one embodiment of the present invention, the above nucleotide sequences are shown in SEQ ID NO.9 to SEQ ID NO.17 or sequences with more than 95% of homology with the amino acid sequences shown in SEQ ID NO.9 to SEQ ID NO.17.

The nucleic acid molecule may be prepared according to the nucleotide sequences in the specification by arbitrary suitable molecular biology method.

The expression vector constructed in step A) may use arbitrary suitable method to construct the nucleotide sequences in the expression vector corresponding to the host cell.

Then, the expression vector is transformed or transfected into the host cell. Preferably, in one embodiment of the present invention, after CHO cell expression vector is constructed, the inventor transfects the expression vector into an HEK293FT cell or CHO cell to construct a recombinant cell line.

The protein expression in step B) may express the recombinant protein according to the used different expression systems. Further, in one embodiment of the present invention, the inventor performs screening with a limited dilution method to obtain a cell line capable of stably secrete and express the RBD trimer protein or the fusion protein.

The purifying in step C) may be an arbitrary suitable method, for example, a salting out method, a precipitation method, dialysis or ultrafiltration, molecular sieve chromatography, ion exchange chromatography, hydrophobic chromatography, affinity chromatography and the like. Preferably, in one embodiment of the present invention, the RBD trimer protein or the fusion protein is purified using ion exchange chromatography and hydrophobic chromatography.

Certainly, according to the prior art, before the purifying step, the preparation method should further include a collection process of target proteins, for example, collection of a cell culture supernatant rich in the target proteins. The process of breaking the host cell after the target proteins are expressed may use, for example, ultrasonic disruption, breaking with repeated freeze thawing, a chemical treatment method or other arbitrary suitable breaking methods. The collection process of the host cell should also be understood as falling within the scope of the purifying.

Another aspect of the present invention provides use of the recombinant SARS-CoV-2 RBD trimer protein, the fusion protein, the nucleic acid molecule, the vector or the host cell to preparation of a drug for treating and/or preventing SARS-CoV-2 infection and/or diseases caused by SARS-CoV-2.

The disease caused by SARS-CoV-2, is preferably, novel coronavirus pneumonia (COVID-19).

Another aspect of the present invention provides a vaccine. The vaccine includes the recombinant SARS-CoV-2 RBD trimer protein or the fusion protein, and the adjuvant.

In the embodiments of the present invention, the vaccine is a recombinant protein vaccine (or called a genetic engineering subunit vaccine). Further, in some other embodiments of the present invention, the vaccine may further be a genetic engineering vector vaccine or a nucleic acid vaccine. The above vaccine includes the nucleotide sequence in this specification or encodes the amino acid sequence in the specification.

The vaccine of the present invention may include an arbitrary suitable adjuvant. However, preferably, in the embodiments of the present invention, the adjuvant is aluminium hydroxide, aluminium phosphate, MF59 or CpG. More preferably, the adjuvant is the aluminium hydroxide.

Another aspect of the present invention provides a method for preparing the vaccine. The recombinant SARS-CoV-2 RBD trimer protein or the fusion protein obtained through purification and the adjuvant are mixed.

Another aspect of the present invention provides use of the vaccine for treating and/or preventing SARS-CoV-2 infection and/or diseases caused by SARS-CoV-2.

The disease caused by SARS-CoV-2, is preferably, novel coronavirus pneumonia (COVID-19).

Another aspect of the present invention provides a drug composition. The drug composition includes the vaccine, and a pharmaceutically acceptable vector.

The pharmaceutically acceptable vector may be an arbitrary pharmaceutically acceptable additive, for example, normal saline, a cell culture medium, glucose, water for injection, glycerol, amino acid, a combination thereof, a stabilizing agent, a surfactant, a preservative, an isotonic agent and the like.

The drug composition provided by the present invention may further be used in combination with other drugs for treating and/or preventing SARS-CoV-2 infection and/or the disease caused by the SARS-CoV-2 with an effective and safe dosage.

Another aspect of the present invention provides a method for eliciting immune response of a subject against various SARS-CoV-2 epidemic strains or treating SARS-CoV-2 infection of a subject, where the vaccine or the drug composition with an effective dose is applied to the subject.

The subject may be a human or other animals.

Application may be intramuscular injection, intraperitoneal injection or subcutaneous injection.

Beneficial Effects of the Present Invention the vaccine prepared by the present invention takes the RBD trimer protein as an antigen and is supplemented with an adjuvant to immunize an organism, so that a high-titer neutralizing antibody aiming at various SARS-CoV-2 epidemic strains can be generated at the same time, and can be used for treating and/or preventing SARS-CoV-2 infection and/or coronavirus disease.

SEQUENCE DESCRIPTION

Figure 1:
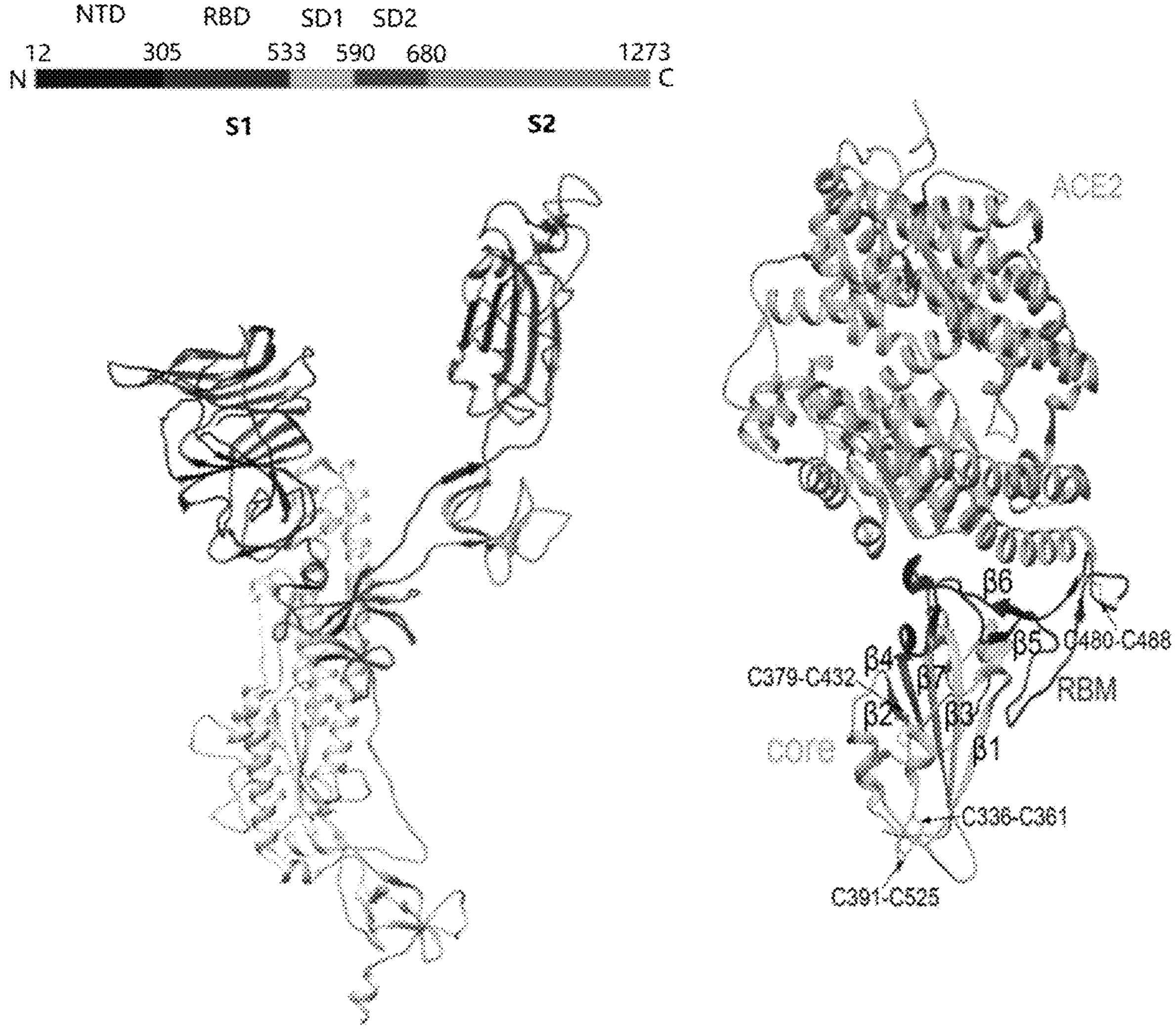
FIG. 1 is structure analysis diagram of an SARS-CoV-2 S protein in Example 1 of the present invention, where A is an S protein monomer structure (drawn using a UCSF Chimera software based on a coordinate file with a PDB code being 6zgg); an S1 structure unit includes NTD, RBD, CTD1 and CTD2 structural domains; and B is a composite structure of the RBD and an ACE2 receptor (drawn using the UCSF Chimera software based on a coordinate file with the PDB code being 6m0j)

SEQ ID NO.1 is an amino acid sequence of one SARS-CoV-2 (prototype strain) RBD in the examples of the present invention:

SEQ ID NO.2 is an amino acid sequence of another SARS-CoV-2 (Beta (B.1.351) mutant strain) RBD in the examples of the present invention;

SEQ ID NO.3 is an amino acid sequence of another SARS-CoV-2 (Kappa(B.1.617.1) mutant strain) RBD in the examples of the present invention;

SEQ ID NO.4 is an amino acid sequence of a trimer protein A in the examples of the present invention;

SEQ ID NO.5 is an amino acid sequence of a trimer protein B in the examples of the present invention;

SEQ ID NO.6 is an amino acid sequence of a trimer protein C in the examples of the present invention;

SEQ ID NO.7 is an amino acid sequence of a trimer protein D in the examples of the present invention;

SEQ ID NO.8 is an amino acid sequence of a trimer protein E in the examples of the present invention;

SEQ ID NO.9 is an optimized nucleotide sequence encoding a trimer protein A in the examples of the present invention;

SEQ ID NO.10 is an optimized nucleotide sequence encoding a trimer protein B in the examples of the present invention;

SEQ ID NO.11 is an optimized nucleotide sequence encoding a trimer protein C in the examples of the present invention;

SEQ ID NO.12 is an optimized nucleotide sequence encoding a trimer protein C in the examples of the present invention;

SEQ ID NO.13 is an optimized nucleotide sequence encoding a trimer protein C in the examples of the present invention;

SEQ ID NO.14 is an optimized nucleotide sequence encoding a trimer protein C in the examples of the present invention;

SEQ ID NO.15 is an optimized nucleotide sequence encoding a trimer protein D in the examples of the present invention;

SEQ ID NO.16 is an optimized nucleotide sequence encoding a trimer protein E in the examples of the present invention;

SEQ ID NO.17 is an optimized nucleotide sequence encoding a trimer protein E in the examples of the present invention;

SEQ ID NO.18 is an amino acid sequence of a trimer protein in the examples of the present invention; and SEQ ID NO.19 is an amino acid sequence of a dimer protein in the examples of the present invention.

SEQUENCE TABLE

| Number | Sequence |
|---|---|
| SEQ ID NO. 1 | RVQPTESIVRFPNITNLCPFGEVFNATRFA<br>SVYAWNRKRISNCVADYSVLYNSASFSTFK<br>CYGVSPTKLNDLCFTNVYADSFVIRGDEVR<br>QIAPGQTGKIADYNYKLPDDFTGCVIAWNS<br>NNLDSKVGGNYNYLYRLFRKSNLKPFERDI<br>STEIYQAGSTPCNGVEGFNCYFPLQSYGFQ<br>PTNGVGYQPYRVVVLSFELLHAPATVCGPK<br>KSTNLVKNK |
| SEQ ID NO. 2 | RVQPTESIVRFPNITNLCPFGEVENATRFA<br>SVYAWNRKRISNCVADYSVLYNSASFSTFK<br>CYGVSPTKLNDLCFTNVYADSFVIRGDEVR<br>QIAPGQTGNIADYNYKLPDDFTGCVIAWNS<br>NNLDSKVGGNYNYLYRLFRKSNLKPFERDI<br>STEIYQAGSTPCNGVKGFNCYFPLQSYGFQ<br>PTYGVGYQPYRVVVLSFELLHAPATVCGPK<br>KSTNLVKNK |
| SEQ ID No. 3 | RVQPTESIVRFPNITNLCPFGEVFNATRFA<br>SVYAWNRKRISNCVADYSVLYNSASFSTFK<br>CYGVSPTKLNDLCFTNVYADSFVIRGDEVR<br>QIAPGQTGKIADYNYKLPDDFTGCVIAWNS<br>NNLDSKVGGNYNYRYRLFRKSNLKPFERDI<br>STEIYQAGSTPCNGVQGFNCYFPLQSYGFQ<br>PTNGVGYQPYRVVVLSFELLHAPATVCGPK<br>KSTNLVKNK |
| SEQ ID No. 4 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGKIADYNYKLPDDFTGCVIAWN<br>SNNLDSKVGGNYNYLYRLFRKSNLKPFERD<br>ISTEIYQAGSTPCNGVEGFNCYFPLQSYGF<br>QPTNGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGNIADYNYKLPDD<br>FTGCVIAWNSNNLDSKVGGNYNYLYRLFRK<br>SNLKPFERDISTEIYQAGSTPCNGVKGFNC<br>YFPLQSYGFQPTYGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND<br>LCFTNVYADSFVIRGDEVRQIAPGQTGKIA<br>DYNYKLPDDFTGCVIAWNSNNLDSKVGGNY<br>NYRYRLFRKSNLKPFERDISTEIYQAGSTP<br>CNGVQGFNCYFPLQSYGFQPTNGVGYQPYR<br>VVVLSFELLHAPATVCGPKKSTNLVKNK |
| SEQ ID No. 5 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGKIADYNYKLPDDFTGCVIAWN<br>SNNLDSKVGGNYNYLYRLFRKSNLKPFERD<br>ISTEIYQAGSTPCNGVEGFNCYFPLQSYGF<br>QPTNGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGNIADYNYKLPDD<br>FTGCVIAWNSNNLDSKVGGNYNYLYRLFRK<br>SNLKPFERDISTEIYQAGSTPCNGVKGFNC<br>YFPLQSYGFQPTYGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND |

-continued

SEQUENCE TABLE

| Number | Sequence |
|---|---|
| | LCFTNVYADSFVIRGDEVRQIAPGQTGKIA<br>DYNYKLPDDFTGCVIAWNSNNLDSKVGGNY<br>NYLYRLFRKSNLKPFERDISTEIYQAGSTP<br>CNGVEGENCYFPLQSYGFQPTNGVGYQPYR<br>VVVLSFELLHAPATVCGPKKSTNLVKNK |
| SEQ ID No. 6 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGKIADYNYKLPDDFTGCVIAWN<br>SNNLDSKVGGNYNYLYRLFRKSNLKPFERD<br>ISTEIYQAGSTPCNGVEGFNCYFPLQSYGF<br>QPTNGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGNIADYNYKLPDD<br>FTGCVIAWNSNNLDSKVGGNYNYLYRLFRK<br>SNLKPFERDISTEIYQAGSTPCNGVKGFNC<br>YFPLQSYGFQPTYGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND<br>LCFTNVYADSFVIRGDEVRQIAPGQTGNIA<br>DYNYKLPDDFTGCVIAWNSNNLDSKVGGNY<br>NYLYRLFRKSNLKPFERDISTEIYQAGSTP<br>CNGVKGFNCYFPLQSYGFQPTYGVGYQPYR<br>VVVLSFELLHAPATVCGPKKSTNLVKNK |
| SEQ ID No. 7 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGNIADYNYKLPDDFTGCVIAWN<br>SNNLDSKVGGNYNYLYRLFRKSNLKPFERD<br>ISTEIYQAGSTPCNGVKGFNCYFPLQSYGF<br>QPTYGVGYQPYRVVVLSFELLHAPATVCGP<br>KKSTNLVKNKRVQPTESIVRFPNITNLCPF<br>GEVENATRFASVYAWNRKRISNCVADYSVL<br>YNSASFSTFKCYGVSPTKLNDLCFTNVYAD<br>SFVIRGDEVRQIAPGQTGKIADYNYKLPDD<br>FTGCVIAWNSNNLDSKVGGNYNYLYRLFRK<br>SNLKPFERDISTEIYQAGSTPCNGVEGENC<br>YFPLQSYGFQPTNGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND<br>LCFTNVYADSFVIRGDEVRQIAPGQTGNIA<br>DYNYKLPDDFTGCVIAWNSNNLDSKVGGNY<br>NYLYRLFRKSNLKPFERDISTEIYQAGSTP<br>CNGVKGFNCYFPLQSYGFQPTYGVGYQPYR<br>VVVLSFELLHAPATVCGPKKSTNLVKNK |
| SEQ ID No. 8 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGNIADYNYKLPDDFTGCVIAWN<br>SNNLDSKVGGNYNYLYRLFRKSNLKPFERD<br>ISTEIYQAGSTPCNGVKGFNCYFPLQSYGF<br>QPTYGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGNIADYNYKLPDD<br>FTGCVIAWNSNNLDSKVGGNYNYLYRLFRK<br>SNLKPFERDISTEIYQAGSTPCNGVKGFNC<br>YFPLQSYGFQPTYGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND<br>LCFTNVYADSFVIRGDEVRQIAPGQTGNIA<br>DYNYKLPDDFTGCVIAWNSNNLDSKVGGNY<br>NYLYRLFRKSNLKPFERDISTEIYQAGSTP<br>CNGVKGFNCYFPLQSYGFQPTYGVGYQPYR<br>VVVLSFELLHAPATVCGPKKSTNLVKNK |

-continued

SEQUENCE TABLE

| Number | Sequence |
|---|---|
| SEQ ID No. 9 | ATGAGAGTGCAGCCTACCGAGAGCATTGTC<br>AGATTCCCTAACATCACCAATCTGTGCCCT<br>TTCGGCGAGGTGTTCAACGCTACAAGATTT<br>GCTAGCGTGTACGCTTGGAACAGAAAGAGA<br>ATCAGCAATTGCGTCGCCGACTACAGCGTG<br>CTGTACAACAGCGCCTCCTTCAGCACCTTC<br>AAGTGCTACGGCGTCAGCCCTACAAAACTG<br>AATGACCTGTGCTTTACAAATGTGTATGCC<br>GATAGCTTCGTCATCAGAGGCGACGAGGTG<br>AGGCAAATCGCTCCTGGCCAAACCGGCAAG<br>ATCGCCGACTACAATTACAAGCTGCCTGAC<br>GATTTCACCGGATGCGTGATTGCCTGGAAC<br>AGCAACAACCTGGACAGCAAGGTGGGCGGC<br>AACTACAACTACCTGTACAGACTGTTTAGA<br>AAAAGCAACCTGAAGCCTTTCGAGAGAGAC<br>ATCAGCACCGAGATCTACCAAGCCGGCAGC<br>ACACCTTGCAACGGCGTGGAGGGATTCAAC<br>TGCTATTTCCCTCTGCAGAGCTACGGCTTT<br>CAGCCTACCAACGGCGTGGGCTATCAGCCT<br>TATAGAGTCGTGGTGCTCAGCTTCGAACTC<br>CTGCACGCCCCTGCTACAGTGTGTGGCCCT<br>AAGAAGTCCACCAACCTGGTGAAGAATAAG<br>AGAGTGCAACCTACCGAGAGCATCGTGAGA<br>TTCCCCAATATTACCAACCTGTGCCCCTTT<br>GGCGAAGTGTTCAACGCCACAAGATTCGCT<br>AGCGTGTACGCCTGGAACAGAAAGAGAATC<br>AGCAACTGCGTGGCCGACTACAGCGTGCTC<br>TACAACTCCGCTAGCTTCAGCACCTTTAAG<br>TGCTACGGCGTGAGCCCTACCAAGCTGAAC<br>GACCTGTGCTTTACCAACGTCTATGCTGAC<br>AGCTTTGTGATCAGAGGCGACGAGGTGAGA<br>CAGATCGCTCCCGGACAGACCGGCAATATC<br>GCCGATTACAACTACAAGCTGCCCGACGAT<br>TTCACCGGATGCGTGATCGCCTGGAACAGC<br>AACAATCTGGACTCCAAGGTGGGAGGCAAT<br>TACAATTACCTGTACAGACTGTTTAGAAAA<br>TCCAACCTGAAGCCTTTCGAGAGAGACATT<br>TCCACCGAGATCTACCAAGCCGGCTCCACA<br>CCTTGCAATGGAGTGAAGGGCTTCAACTGC<br>TACTTCCCTCTGCAGAGCTACGGCTTTCAG<br>CCTACATACGGAGTCGGCTATCAGCCTTAC<br>AGAGTCGTCGTCCTGAGCTTCGAGCTCCTG<br>CACGCCCCCGCCACCGTCTGCGGACCTAAG<br>AAGTCCACAAACCTCGTCAAAAACAAGAGA<br>GTGCAGCCTACCGAGAGCATCGTGAGGTTT<br>CCTAACATCACCAACCTGTGCCCTTTCGGC<br>GAGGTCTTTAACGCCACAAGATTCGCTAGC<br>GTCTACGCCTGGAACAGAAAGAGGATTAGC<br>AATTGTGTCGCCGACTACAGCGTGCTGTAC<br>AACAGCGCTAGCTTCAGCACCTTCAAGTGC<br>TACGGCGTGAGCCCTACCAAGCTGAACGAC<br>CTGTGCTTTACAAACGTGTATGCCGACAGC<br>TTCGTGATTAGGGGCGACGAGGTGAGGCAA<br>ATCGCTCCTGGCCAAACCGGCAAGATCGCC<br>GACTACAACTACAAGCTGCCTGACGATTTC<br>ACCGGCTGCGTGATCGCCTGGAACAGCAAC<br>AACCTGGATAGCAAGGTGGGCGGCAATTAC<br>AACTACAGATATAGACTGTTCAGAAAGAGC<br>AACCTGAAGCCTTTCGAGAGAGACATCTCC<br>ACCGAGATCTATCAAGCCGGCAGCACACCT<br>TGCAACGGAGTGCAAGGCTTCAACTGCTAT<br>TTCCCTCTGCAATCCTACGGCTTTCAGCCT<br>ACCAACGGAGTGGGCTATCAGCCTTACAGA<br>GTCGTCGTGCTGAGCTTCGAGCTGCTGCAC<br>GCCCCTGCCACAGTGTGCGGACCTAAAAAG<br>AGCACAAATCTGGTGAAGAACAAGTGA |
| SEQ ID No. 10 | ATGAGAGTGCAGCCTACAGAGAGCATTGTG<br>AGATTCCCTAACATCACAAACCTGTGCCCT<br>TTCGGCGAGGTGTTCAACGCCACAAGATTC<br>GCTAGCGTGTACGCCTGGAACAGAAAAAGA<br>ATTAGCAATTGCGTCGCCGATTACAGCGTG<br>CTGTATAACAGCGCTTCCTTCAGCACCTTC<br>AAGTGCTACGGCGTCAGCCCTACAAAGCTG<br>AACGACCTGTGCTTCACAAACGTGTATGCC<br>GACAGCTTCGTGATCAGAGGCGACGAGGTG<br>AGGCAAATCGCTCCTGGCCAAACCGGCAAG<br>ATCGCCGACTACAATTACAAGCTGCCTGAT<br>GACTTCACCGGATGCGTGATTGCCTGGAAC<br>AGCAACAACCTGGACAGCAAAGTCGGAGGA<br>AACTACAACTACCTGTACAGACTGTTCAGA<br>AAGAGCAACCTGAAGCCTTTCGAGAGAGAC<br>ATCAGCACCGAGATCTACCAAGCCGGCTCC<br>ACACCTTGCAACGGCGTGGAGGGATTCAAC<br>TGCTACTTCCCTCTGCAGAGCTACGGCTTT<br>CAGCCCACCAACGGCGTGGGCTATCAGCCT<br>TACAGAGTGGTCGTCCTGAGCTTTGAGCTG<br>CTCCACGCCCCTGCCACCGTCTGCGGCCCC<br>AAAAAAAGCACCAATCTGGTGAAGAACAAG<br>AGGGTGCAGCCTACAGAGAGCATCGTGAGA<br>TTCCCTAACATTACCAACCTGTGCCCTTTC<br>GGAGAAGTGTTTAACGCCACAAGATTCGCC<br>TCCGTCTACGCTTGGAATAGAAAGAGGATC<br>AGCAACTGCGTGGCCGACTACAGCGTGCTG<br>TACAATTCCGCCTCCTTCAGCACCTTCAAG<br>TGTTACGGCGTGAGCCCTACCAAGCTGAAC<br>GACCTGTGCTTCACCAACGTGTACGCCGAT<br>AGCTTCGTGATTAGAGGCGACGAGGTGAGG<br>CAGATCGCCCCTGGACAAACCGGCAACATT<br>GCTGACTACAATTACAAGCTGCCTGACGAC<br>TTCACCGGCTGCGTGATCGCCTGGAACAGC<br>AACAACCTGGACAGCAAGGTCGGAGGCAAT<br>TACAATTACCTCTATAGACTGTTCAGAAAA<br>AGCAATCTCAAGCCTTTCGAAAGAGACATT<br>AGCACCGAGATCTACCAAGCCGGCAGCACC<br>CCCTGCAACGGCGTGAAAGGATTCAACTGC<br>TACTTCCCCCTGCAGAGCTACGGCTTTCAG<br>CCCACCTACGGAGTGGGCTATCAACCCTAC<br>AGAGTGGTCGTGCTCTCCTTCGAGCTGCTG<br>CATGCCCCTGCCACAGTGTGCGGACCTAAA<br>AAGTCCACCAACCTCGTGAAGAACAAGAGA<br>GTGCAGCCTACAGAGAGCATCGTGAGGTTC<br>CCCAACATCACCAACCTGTGCCCTTTCGGC<br>GAGGTGTTTAACGCTACAAGATTCGCTAGC<br>GTGTACGCTTGGAACAGAAAGAGAATCTCC<br>AATTGCGTGGCCGACTACAGCGTGCTGTAC<br>AACAGCGCTAGCTTCAGCACCTTCAAGTGC<br>TACGGAGTGTCCCCTACCAAGCTGAACGAC<br>CTGTGCTTCACCAACGTGTACGCCGATAGC<br>TTCGTGATTAGAGGAGACGAAGTGAGACAG<br>ATTGCTCCTGGACAGACCGGCAAGATCGCC<br>GACTACAATTACAAGCTGCCTGATGACTTT<br>ACCGGCTGTGTGATTGCCTGGAACAGCAAC<br>AACCTGGACAGCAAGGTGGGCGGCAACTAC<br>AACTATCTGTACAGACTCTTCAGAAAGAGC<br>AATCTGAAGCCTTTTGAAAGGGACATCAGC<br>ACCGAGATCTATCAAGCCGGCAGCACCCCT<br>TGCAACGGAGTCGAGGGCTTCAACTGCTAC<br>TTTCCTCTGCAGAGCTATGGCTTTCAGCCT<br>ACCAACGGCGTCGGATATCAGCCTTACAGA<br>GTCGTGGTGCTGAGCTTCGAGCTGCTCCAC<br>GCCCCTGCCACCGTCTGCGGCCCTAAGAAA<br>AGCACCAACCTGGTCAAGAACAAATGA |
| SEQ ID No. 11 | ATGAGAGTGCAGCCTACAGAGAGCATTGTG<br>AGATTCCCTAACATCACCAATCTGTGCCCT<br>TTCGGCGAGGTGTTCAACGCCACAAGATTC<br>GCTAGCGTGTACGCCTGGAACAGAAAGAGG<br>ATCTCCAATTGCGTGGCTGACTATAGCGTG<br>CTGTACAATAGCGCTAGCTTCAGCACCTTC<br>AAGTGCTACGGCGTCAGCCCTACAAAGCTG<br>AACGACCTGTGCTTCACAAACGTGTATGCC<br>GACAGCTTCGTGATCAGAGGCGACGAGGTG<br>AGGCAAATCGCTCCTGGCCAAACCGGCAAG<br>ATCGCCGACTATAATTATAAGCTGCCTGAT<br>GACTTCACCGGCTGCGTCATCGCCTGGAAC<br>AGCAATAATCTGGACAGCAAGGTCGGAGGC<br>AACTACAACTACCTGTACAGACTGTTCAGA<br>AAGAGCAACCTGAAGCCTTTCGAGAGAGAC<br>ATCAGCACCGAGATTTACCAAGCCGGCTCC |

-continued

SEQUENCE TABLE

| Number | Sequence |
|---|---|
| | ACCCCTTGCAACGGCGTGGAAGGCTTCAAC<br>TGCTACTTCCCTCTGCAGTCCTACGGCTTT<br>CAGCCTACAAACGGCGTGGGCTACCAACCC<br>TACAGAGTCGTGGTGCTCAGCTTCGAGCTG<br>CTGCATGCCCCTGCTACCGTGTGCGGCCCC<br>AAAAAGAGCACCAACCTCGTGAAGAATAAG<br>AGAGTGCAGCCTACCGAGAGCATCGTCAGA<br>TTCCCTAACATCACCAATCTCTGCCCCTTC<br>GGCGAGGTGTTCAACGCCACAAGATTCGCT<br>AGCGTCTACGCTTGGAATAGAAAGAGAATC<br>AGCAACTGTGTGGCCGACTATAGCGTGCTG<br>TACAACAGCGCTAGCTTTAGCACCTTTAAG<br>TGCTACGGCGTGTCCCCTACCAAGCTGAAC<br>GACCTGTGCTTCACAAATGTGTACGCCGAC<br>AGCTTCGTGATCAGAGGAGACGAGGTGAGG<br>CAGATCGCCCCTGGACAAACCGGCAATATT<br>GCCGACTACAACTACAAGCTGCCCGACGAC<br>TTCACCGGCTGCGTGATCGCCTGGAACAGC<br>AACAACCTCGACAGCAAAGTGGGAGGCAAT<br>TACAACTACCTGTATAGACTGTTTAGAAAG<br>AGCAACCTGAAGCCTTTCGAGAGGGACATC<br>TCCACCGAGATCTACCAAGCCGGCAGCACC<br>CCTTGTAACGGCGTGAAGGGCTTCAACTGT<br>TACTTCCCTCTGCAGAGCTATGGCTTTCAG<br>CCTACATACGGAGTGGGCTATCAGCCTTAC<br>AGAGTGGTGGTCCTCTCCTTTGAACTCCTG<br>CATGCCCCTGCCACAGTGTGCGGACCTAAA<br>AAGAGCACCAACCTCGTGAAGAATAAGAGA<br>GTGCAGCCTACCGAGAGCATCGTGAGATTC<br>CCCAATATCACCAACCTGTGTCCTTTCGGC<br>GAGGTGTTCAATGCCACAAGATTCGCTAGC<br>GTCTATGCCTGGAACAGAAAGAGAATCTCC<br>AATTGCGTGGCCGACTACAGCGTGCTGTAC<br>AACAGCGCTAGCTTCAGCACCTTCAAGTGC<br>TACGGAGTGAGCCCTACCAAGCTGAACGAC<br>CTCTGCTTTACCAATGTGTACGCCGATAGC<br>TTCGTCATTAGAGGAGACGAGGTGAGACAG<br>ATTGCTCCTGGACAGACCGGCAACATCGCC<br>GACTACAACTACAAGCTGCCTGACGATTTT<br>ACCGGCTGTGTGATCGCCTGGAACAGCAAC<br>AACCTGGACAGCAAGGTCGGCGGCAACTAC<br>AACTATCTGTACAGACTGTTTAGAAAGAGC<br>AACCTGAAGCCTTTCGAAAGGGACATCAGC<br>ACCGAGATCTATCAAGCCGGCTCCACCCCT<br>TGCAACGGCGTCAAGGGCTTTAACTGCTAC<br>TTCCCTCTGCAGAGCTACGGCTTTCAGCCT<br>ACCTACGGCGTCGGATATCAGCCTTATAGA<br>GTGGTCGTGCTGAGCTTCGAGCTGCTCCAC<br>GCCCCTGCCACCGTCTGCGGCCCTAAAAAG<br>AGCACCAACCTGGTCAAGAACAAATGA |
| SEQ ID No. 12 | ATGAGAGTGCAGCCCACAGAGAGCATTGTG<br>AGATTCCCCAACATCACCAATCTGTGCCCC<br>TTCGGCGAGGTGTTCAACGCCACAAGATTC<br>GCTAGCGTGTACGCCTGGAACAGAAAGCGG<br>ATCTCCAATTGCGTGGCTGACTATAGCGTG<br>CTGTACAATAGCGCTAGCTTCAGCACCTTC<br>AAGTGCTACGGCGTCAGCCCCACAAAGCTG<br>AACGACCTGTGCTTCACAAACGTGTATGCC<br>GACAGCTTCGTGATCAGAGGCGACGAGGTG<br>CGGCAAATCGCTCCCGGCCAAACCGGCAAG<br>ATCGCCGACTATAATTATAAGCTGCCCGAT<br>GACTTCACCGGCTGCGTCATCGCCTGGAAC<br>AGCAATAATCTGGACAGCAAGGTCGGGGGC<br>AACTACAACTACCTGTACAGACTGTTCAGA<br>AAGAGCAACCTGAAGCCCTTCGAGAGAGAC<br>ATCAGCACCGAGATTTACCAAGCCGGCTCC<br>ACCCCCTGCAACGGCGTGGAAGGCTTCAAC<br>TGCTACTTCCCCCTGCAGTCCTACGGCTTT<br>CAGCCCACAAACGGCGTGGGCTACCAACCT<br>TACAGAGTCGTGGTGCTCAGCTTCGAGCTG<br>CTGCATGCCCCCGCTACCGTGTGCGGCCCT<br>AAAAAGAGCACCAACCTCGTGAAGAATAAG<br>AGAGTGCAGCCCACCGAGAGCATCGTCAGA<br>TTCCCCAACATCACCAATCTCTGCCCTTTC<br>GGCGAGGTGTTCAACGCCACAAGATTCGCT<br>AGCGTCTACGCTTGGAACCGGAAGAGAATC<br>AGCAACTGTGTGGCCGACTATAGCGTGCTG<br>TACAACAGCGCTAGCTTTAGCACCTTTAAG<br>TGCTACGGCGTGTCCCCCACCAAGCTGAAC<br>GACCTGTGCTTCACAAATGTGTACGCCGAC<br>AGCTTCGTGATCAGAGGGGACGAGGTGCGG<br>CAGATCGCCCCCGGGCAAACCGGCAATATT<br>GCCGACTACAACTACAAGCTGCCTGACGAC<br>TTCACCGGCTGCGTGATCGCCTGGAACAGC<br>AACAACCTCGACAGCAAAGTGGGGGGCAAT<br>TACAACTACCTGTATAGACTGTTTAGAAAG<br>AGCAACCTGAAGCCCTTCGAGCGGGACATC<br>TCCACCGAGATCTACCAAGCCGGCAGCACC<br>CCCTGTAACGGCGTGAAGGGCTTCAACTGT<br>TACTTCCCCCTGCAGAGCTATGGCTTTCAG<br>CCCACATACGGGGTGGGCTATCAGCCCTAC<br>AGAGTGGTGGTCCTCTCCTTTGAACTCCTG<br>CATGCCCCCGCCACAGTGTGCGGGCCCAAA<br>AAGAGCACCAACCTCGTGAAGAATAAGAGA<br>GTGCAGCCCACCGAGAGCATCGTGAGATTC<br>CCTAATATCACCAACCTGTGTCCCTTCGGC<br>GAGGTGTTCAATGCCACAAGATTCGCTAGC<br>GTCTATGCCTGGAACAGAAAGAGAATCTCC<br>AATTGCGTGGCCGACTACAGCGTGCTGTAC<br>AACAGCGCTAGCTTCAGCACCTTCAAGTGC<br>TACGGGGTGAGCCCCACCAAGCTGAACGAC<br>CTCTGCTTTACCAATGTGTACGCCGATAGC<br>TTCGTCATCCGGGGGGACGAGGTGAGACAG<br>ATTGCTCCCGGGCAGACCGGCAACATCGCC<br>GACTACAACTACAAGCTGCCCGACGATTTT<br>ACCGGCTGTGTGATCGCCTGGAACAGCAAC<br>AACCTGGACAGCAAGGTCGGCGGCAACTAC<br>AACTATCTGTACAGACTGTTTAGAAAGAGC<br>AACCTGAAGCCCTTCGAACGGGACATCAGC<br>ACCGAGATCTATCAAGCCGGCTCCACCCCC<br>TGCAACGGCGTCAAGGGCTTTAACTGCTAC<br>TTCCCCCTGCAGAGCTACGGCTTTCAGCCC<br>ACCTACGGCGTCGGGTATCAGCCCTACCGG<br>GTGGTCGTGCTGAGCTTCGAGCTGCTCCAC<br>GCCCCCGCCACCGTCTGCGGCCCCAAAAAG<br>AGCACCAACCTGGTCAAGAACAAATGA |
| SEQ ID No. 13 | ATGAGAGTGCAGCCTACCGAGAGCATCGTG<br>AGATTTCCTAATATCACCAATCTCTGCCCC<br>TTCGGCGAGGTGTTTAACGCCACAAGATTT<br>GCTAGCGTGTACGCCTGGAACAGAAAAAGA<br>ATCTCCAACTGCGTGGCCGACTACAGCGTC<br>CTGTACAATAGCGCTAGCTTCAGCACCTTC<br>AAGTGCTACGGCGTCTCCCCTACAAAGCTG<br>AATGACCTGTGTTTTACCAACGTGTATGCC<br>GACAGCTTCGTGATTAGAGGCGATGAGGTG<br>AGGCAGATCGCCCCTGGACAGACCGGCAAG<br>ATCGCTGATTACAACTACAAGCTGCCTGAC<br>GACTTCACCGGCTGCGTGATCGCCTGGAAC<br>AGCAACAACCTGGATAGCAAGGTGGGCGGC<br>AACTACAACTATCTGTACAGACTGTTCAGA<br>AAAAGCAACCTGAAGCCTTTTGAGAGAGAC<br>ATCAGCACAGAGATCTACCAAGCCGGCAGC<br>ACCCCTTGCAACGGCGTGGAAGGATTTAAC<br>TGCTATTTCCCTCTGCAGAGCTATGGCTTC<br>CAACCTACCAACGGAGTGGGCTATCAGCCC<br>TACAGAGTGGTCGTGCTGAGCTTCGAGCTG<br>CTGCACGCTCCTGCCACCGTGTGCGGCCCC<br>AAAAAGTCCACCAACCTGGTGAAGAATAAA<br>AGAGTGCAGCCTACCGAATCCATCGTGAGA<br>TTCCCTAACATCACCAACCTGTGCCCTTTC<br>GGCGAGGTCTTCAACGCCACAAGATTTGCT<br>AGCGTGTACGCCTGGAACAGAAAGAGAATC<br>AGCAACTGCGTGGCCGACTACAGCGTCCTG<br>TACAACAGCGCCTCCTTCAGCACCTTCAAA<br>TGCTACGGCGTGTCCCCTACCAAGCTGAAT<br>GACCTGTGCTTTACCAACGTGTACGCCGAC<br>AGCTTTGTGATCAGAGGCGACGAGGTGAGA<br>CAGATTGCTCCTGGACAGACCGGCAACATT |

-continued

SEQUENCE TABLE

| Number | Sequence |
| --- | --- |
| | GCCGATTACAATTACAAGCTGCCTGATGAT<br>TTCACCGGCTGTGTGATCGCCTGGAACAGC<br>AACAACCTGGACAGCAAGGTGGGCGGCAAC<br>TATAATTACCTGTATAGACTGTTCAGAAAA<br>AGCAACCTGAAGCCTTTCGAGAGAGACATC<br>TCCACCGAAATTTACCAAGCCGGATCCACA<br>CCTTGCAACGGCGTGAAGGGCTTCAATTGT<br>TACTTCCCTCTGCAAAGCTACGGCTTTCAG<br>CCTACATACGGAGTGGGCTACCAACCCTAC<br>AGAGTGGTCGTGCTGAGCTTCGAGCTGCTC<br>CACGCCCCTGCCACCGTGTGCGGCCCTAAA<br>AAGAGCACCAACCTGGTGAAGAATAAGAGA<br>GTGCAACCCACAGAGAGCATTGTGAGATTC<br>CCTAACATCACAAATCTGTGCCCTTTCGGC<br>GAGGTGTTCAACGCCACAAGATTCGCTAGC<br>GTGTACGCTTGGAACAGAAAGAGAATCAGC<br>AACTGTGTGGCTGACTACAGCGTGCTCTAC<br>AACAGCGCTTCCTTCAGCACCTTTAAATGC<br>TACGGCGTGAGCCCCACAAAGCTCAACGAC<br>CTGTGCTTCACCAACGTCTACGCCGACAGC<br>TTCGTGATTAGAGGAGACGAAGTGAGACAG<br>ATCGCTCCTGGACAGACCGGCAATATCGCC<br>GACTACAACTACAAACTGCCTGACGACTTC<br>ACCGGCTGCGTGATCGCCTGGAACAGCAAT<br>AATCTCGACAGCAAGGTCGGCGGCAACTAC<br>AATTACCTGTATAGACTGTTTAGAAAGAGC<br>AACCTGAAGCCCTTCGAGAGAGACATCTCC<br>ACCGAGATCTACCAAGCCGGCTCCACACCT<br>TGCAACGGCGTGAAGGGCTTCAACTGCTAC<br>TTCCCTCTGCAGAGCTACGGCTTCCAACCT<br>ACCTACGGAGTGGGCTATCAGCCTTATAGA<br>GTGGTCGTGCTGAGCTTCGAACTGCTGCAC<br>GCCCCCGCCACCGTGTGCGGCCCCAAAAAG<br>AGCACAAACCTGGTGAAGAACAAGTGA |
| SEQ ID No. 14 | ATGAGAGTGCAGCCTACCGAGAGCATCGTG<br>AGATTCCCTAACATCACAAACCTCTGCCCT<br>TTTGGAGAGGTCTTCAACGCCACAAGATTC<br>GCCTCCGTGTATGCCTGGAACAGAAAGAGA<br>ATCAGCAATTGCGTGGCTGACTACAGCGTG<br>CTGTACAACTCCGCTAGCTTTAGCACCTTC<br>AAGTGCTACGGCGTGAGCCCTACCAAACTC<br>AACGATCTGTGCTTTACCAACGTCTATGCC<br>GACAGCTTTGTGATCAGAGGCGACGAGGTC<br>AGACAAATCGCCCCCGGACAGACCGGCAAG<br>ATCGCCGACTACAACTATAAACTGCCTGAC<br>GACTTCACCGGCTGCGTGATCGCCTGGAAC<br>AGCAACAACCTGGACTCCAAGGTGGGCGGC<br>AACTACAACTACCTGTACAGACTCTTCAGA<br>AAGAGCAACCTGAAACCTTTCGAAAGAGAC<br>ATCAGCACCGAAATCTACCAAGCCGGCAGC<br>ACCCCTTGCAACGGCGTGGAGGGCTTTAAT<br>TGCTACTTTCCTCTGCAAAGCTACGGCTTT<br>CAGCCCACCAACGGAGTGGGCTATCAGCCT<br>TATAGAGTCGTCGTGCTGAGCTTTGAGCTG<br>CTGCACGCCCCTGCCACCGTCTGCGGCCCT<br>AAAAAGAGCACAAATCTGGTCAAGAACAAG<br>AGAGTGCAGCCTACCGAGAGCATTGTGAGA<br>TTTCCTAACATCACCAATCTGTGCCCTTTC<br>GGCGAGGTGTTCAATGCCACAAGATTTGCT<br>AGCGTCTACGCCTGGAACAGAAAAAGAATC<br>AGCAACTGCGTGGCCGACTACAGCGTGCTG<br>TACAACTCCGCTAGCTTCAGCACCTTTAAG<br>TGCTACGGCGTCAGCCCTACCAAACTGAAC<br>GACCTCTGCTTTACCAACGTGTATGCCGAC<br>AGCTTCGTGATCAGAGGAGACGAGGTGAGA<br>CAGATCGCCCCTGGACAGACCGGCAACATC<br>GCCGATTACAATTACAAACTGCCCGACGAC<br>TTCACCGGCTGTGTGATTGCTTGGAACTCC<br>AACAACCTCGACAGCAAGGTGGGCGGCAAC<br>TACAACTACCTGTATAGACTGTTCAGAAAG<br>AGCAACCTGAAGCCTTTCGAGAGAGATATC<br>AGCACCGAGATCTACCAAGCCGGCAGCACA<br>CCTTGTAACGGCGTGAAAGGCTTCAATTGT<br>TATTTCCCCCTGCAGAGCTACGGCTTTCAG |

-continued

SEQUENCE TABLE

| Number | Sequence |
| --- | --- |
| | CCTACCTATGGCGTGGGATACCAACCTTAC<br>AGAGTGGTCGTGCTGAGCTTCGAACTGCTG<br>CACGCCCCTGCCACCGTGTGCGGCCCCAAA<br>AAGAGCACCAATCTGGTGAAGAACAAAAGA<br>GTGCAACCTACCGAGAGCATCGTGAGATTC<br>CCCAATATTACAAACCTGTGCCCCTTTGGC<br>GAGGTGTTCAACGCCACAAGATTCGCTAGC<br>GTGTACGCCTGGAACAGAAAGAGAATCAGC<br>AACTGCGTGGCTGACTACAGCGTGCTGTAC<br>AACAGCGCCTCCTTCAGCACATTCAAGTGC<br>TACGGAGTCAGCCCTACCAAGCTGAATGAT<br>CTGTGTTTCACAAACGTGTACGCCGACAGC<br>TTCGTGATCAGAGGCGACGAAGTGAGACAG<br>ATTGCCCCTGGACAGACCGGCAACATCGCC<br>GACTACAATTACAAGCTGCCTGACGATTTC<br>ACCGGCTGCGTCATCGCCTGGAACAGCAAC<br>AACCTGGACTCCAAAGTGGGCGGCAACTAC<br>AATTACCTGTATAGACTGTTCAGAAAGTCC<br>AATCTCAAGCCCTTCGAGAGAGACATCAGC<br>ACCGAGATTTATCAAGCCGGCAGCACCCCT<br>TGCAATGGAGTGAAAGGCTTCAACTGCTAC<br>TTCCCTCTGCAGAGCTACGGATTTCAGCCT<br>ACCTACGGAGTGGGCTATCAGCCTTACAGA<br>GTGGTCGTGCTGAGCTTTGAGCTGCTGCAC<br>GCTCCTGCCACCGTGTGCGGCCCTAAAAAG<br>AGCACCAACCTGGTGAAGAACAAGTGA |
| SEQ ID No. 15 | ATGAGAGTGCAGCCTACAGAGAGCATTGTG<br>AGATTCCCTAACATCACAAACCTGTGCCCT<br>TTCGGCGAGGTGTTCAACGCCACAAGATTC<br>GCTAGCGTGTACGCCTGGAACAGAAAAAGA<br>ATTAGCAATTGCGTCGCCGATTACAGCGTG<br>CTGTATAACAGCGCTTCCTTCAGCACCTTC<br>AAGTGCTACGGCGTCAGCCCTACAAAGCTG<br>AACGACCTGTGCTTCACAAACGTGTATGCC<br>GACAGCTTCGTGATCAGAGGCGACGAGGTG<br>AGGCAAATCGCTCCTGGCCAAACCGGCAAC<br>ATCGCCGACTACAATTACAAGCTGCCTGAT<br>GACTTCACCGGATGCGTGATTGCCTGGAAC<br>AGCAACAACCTGGACAGCAAAGTCGGAGGA<br>AACTACAACTACCTGTACAGACTGTTCAGA<br>AAGAGCAACCTGAAGCCTTTCGAGAGAGAC<br>ATCAGCACCGAGATCTACCAAGCCGGCTCC<br>ACACCTTGCAACGGCGTGAAGGGATTCAAC<br>TGCTACTTCCCTCTGCAGAGCTACGGCTTT<br>CAGCCCACCTACGGCGTGGGCTATCAGCCT<br>TACAGAGTGGTCGTCCTGAGCTTTGAGCTG<br>CTCCACGCCCCTGCCACCGTCTGCGGCCCC<br>AAAAAAAGCACCAATCTGGTGAAGAACAAG<br>AGGGTGCAGCCTACAGAGAGCATCGTGAGA<br>TTCCCTAACATTACCAACCTGTGCCCTTTC<br>GGAGAAGTGTTTAACGCCACAAGATTCGCC<br>TCCGTCTACGCTTGGAATAGAAAGAGGATC<br>AGCAACTGCGTGGCCGACTACAGCGTGCTG<br>TACAATTCCGCCTCCTTCAGCACCTTCAAG<br>TGTTACGGCGTGAGCCCTACCAAGCTGAAC<br>GACCTGTGCTTCACCAACGTGTACGCCGAT<br>AGCTTCGTGATTAGAGGCGACGAGGTGAGG<br>CAGATCGCCCCTGGACAAACCGGCAAGATT<br>GCTGACTACAATTACAAGCTGCCTGACGAC<br>TTCACCGGCTGCGTGATCGCCTGGAACAGC<br>AACAACCTGGACAGCAAGGTCGGAGGCAAT<br>TACAATTACCTCTATAGACTGTTCAGAAAA<br>AGCAATCTCAAGCCTTTCGAAAGAGACATT<br>AGCACCGAGATCTACCAAGCCGGCAGCACC<br>CCCTGCAACGGCGTGGAAGGATTCAACTGC<br>TACTTCCCCCTGCAGAGCTACGGCTTTCAG<br>CCCACCAACGGAGTGGGCTATCAACCCTAC<br>AGAGTGGTCGTGCTCTCCTTCGAGCTGCTG<br>CATGCCCCTGCCACAGTGTGCGGACCTAAA<br>AAGTCCACCAACCTCGTGAAGAACAAGAGA<br>GTGCAGCCTACAGAGAGCATCGTGAGGTTC<br>CCCAACATCACCAACCTGTGCCCTTTCGGC<br>GAGGTGTTTAACGCTACAAGATTCGCTAGC<br>GTGTACGCTTGGAACAGAAAGAGAATCTCC |

-continued

SEQUENCE TABLE

| Number | Sequence |
|---|---|
| | AATTGCGTGGCCGACTACAGCGTGCTGTAC<br>AACAGCGCTAGCTTCAGCACCTTCAAGTGC<br>TACGGAGTGTCCCCTACCAAGCTGAACGAC<br>CTGTGCTTCACCAACGTGTACGCCGATAGC<br>TTCGTGATTAGAGGAGACGAAGTGAGACAG<br>ATTGCTCCTGGACAGACCGGCAACATCGCC<br>GACTACAATTACAAGCTGCCTGATGACTTT<br>ACCGGCTGTGTGATTGCCTGGAACAGCAAC<br>AACCTGGACAGCAAGGTGGGCGGCAACTAC<br>AACTATCTGTACAGACTCTTCAGAAAGAGC<br>AATCTGAAGCCTTTTGAAAGGGACATCAGC<br>ACCGAGATCTATCAAGCCGGCAGCACCCCT<br>TGCAACGGAGTCAAGGGCTTCAACTGCTAC<br>TTTCCTCTGCAGAGCTATGGCTTTCAGCCT<br>ACCTACGGCGTCGGATATCAGCCTTACAGA<br>GTCGTGGTGCTGAGCTTCGAGCTGCTCCAC<br>GCCCCTGCCACCGTCTGCGGCCCTAAGAAA<br>AGCACCAACCTGGTCAAGAACAAATGA |
| SEQ ID No. 16 | ATGAGGGTGCAGCCCACAGAGAGCATCGTC<br>AGATTCCCTAACATCACAAACCTGTGTCCT<br>TTTGGCGAGGTCTTCAACGCCACAAGATTC<br>GCTAGCGTGTACGCCTGGAATAGAAAAAGG<br>ATTAGCAACTGTGTGGCTGACTACAGCGTC<br>CTGTATAACAGCGCTTCCTTTTCCACCTTT<br>AAGTGTTATGGCGTGTCCCCCACAAAGCTG<br>AACGACCTGTGTTTTACCAATGTGTACGCC<br>GACAGCTTCGTCATCAGAGGAGACGAGGTG<br>AGACAAATCGCCCCTGGACAGACCGGCAAC<br>ATCGCCGACTACAATTATAAGCTGCCTGAC<br>GACTTTACCGGCTGCGTGATTGCTTGGAAC<br>TCCAACAACCTGGATAGCAAGGTGGGAGGA<br>AACTACAACTACCTCTACAGACTCTTCAGA<br>AAGAGCAATCTGAAGCCTTTCGAGAGAGAT<br>ATCTCCACAGAGATCTATCAAGCCGGCAGC<br>ACCCCTTGTAACGGAGTGAAGGGATTCAAT<br>TGTTATTTCCCTCTGCAAAGCTATGGATTT<br>CAGCCTACCTACGGAGTGGGATATCAGCCC<br>TATAGAGTGGTCGTGCTGAGCTTCGAGCTC<br>CTGCACGCCCCTGCTACAGTCTGTGGCCCT<br>AAGAAGTCCACAAACCTCGTGAAGAACAAG<br>AGAGTGCAGCCTACCGAGAGCATCGTGAGG<br>TTCCCTAACATTACCAACCTCTGTCCTTTT<br>GGAGAAGTCTTTAATGCCACAAGATTTGCT<br>AGCGTGTACGCTTGGAATAGAAAGAGGATT<br>TCCAATTGCGTGGCCGACTACTCCGTCCTG<br>TACAACAGCGCTAGCTTCAGCACCTTCAAA<br>TGCTACGGAGTGAGCCCTACCAAGCTCAAC<br>GACCTGTGCTTTACCAACGTGTACGCTGAC<br>AGCTTCGTCATTAGGGGAGACGAGGTGAGG<br>CAGATCGCTCCTGGACAGACCGGCAACATC<br>GCCGACTACAACTACAAGCTGCCCGACGAT<br>TTCACCGGCTGCGTCATTGCCTGGAATAGC<br>AACAATCTGGACAGCAAGGTGGGAGGAAAC<br>TATAATTACCTGTACAGACTGTTTAGGAAA<br>AGCAACCTCAAACCCTTCGAAAGAGACATT<br>AGCACAGAGATCTACCAAGCCGGCTCCACC<br>CCCTGCAATGGCGTGAAGGGATTTAATTGT<br>TACTTCCCCCTGCAGAGCTATGGCTTTCAA<br>CCTACCTACGGCGTGGGCTATCAGCCCTAT<br>AGGGTGGTGGTCCTCAGCTTTGAACTCCTG<br>CACGCTCCTGCCACCGTGTGCGGCCCCAAA<br>AAGAGCACCAATCTGGTCAAGAACAAGAGA<br>GTGCAGCCCACAGAGTCCATCGTGAGATTT<br>CCTAATATTACCAACCTGTGCCCTTTCGGA<br>GAGGTGTTTAATGCTACAAGATTTGCTAGC<br>GTCTATGCCTGGAACAGAAAGAGAATCAGC<br>AACTGCGTGGCCGATTACAGCGTCCTGTAC<br>AATAGCGCTTCCTTCTCCACCTTTAAATGC<br>TACGGCGTGAGCCCCACCAAGCTGAATGAC<br>CTCTGTTTCACCAACGTGTATGCCGACTCC<br>TTTGTGATTAGAGGAGATGAGGTGAGACAG<br>ATCGCCCCTGGACAAACCGGCAACATTGCC<br>GATTACAATTACAAGCTGCCTGATGACTTC<br>ACCGGCTGTGTGATTGCCTGGAACAGCAAT<br>AACCTGGACAGCAAGGTGGGCGGCAATTAT<br>AACTACCTGTATAGACTGTTCAGAAAGAGC<br>AACCTGAAGCCTTTTGAGAGAGACATCAGC<br>ACCGAGATTTACCAAGCCGGCTCCACCCCT<br>TGCAACGGCGTGAAGGGCTTCAATTGCTAC<br>TTCCCTCTGCAGTCCTACGGCTTTCAGCCT<br>ACATACGGCGTGGGATATCAGCCTTATAGA<br>GTCGTGGTGCTCAGCTTCGAGCTGCTGCAC<br>GCCCCCGCTACAGTGTGTGGACCTAAAAAG<br>TCCACCAATCTCGTCAAGAATAAGTGA |
| SEQ ID No. 17 | ATGAGAGTGCAGCCTACCGAGAGCATCGTG<br>AGATTCCCTAACATCACCAACCTCTGCCCT<br>TTCGGAGAGGTCTTCAACGCCACAAGATTT<br>GCTAGCGTGTACGCCTGGAACAGAAAAAGA<br>ATCTCCAACTGCGTGGCCGACTACAGCGTC<br>CTGTACAATAGCGCTAGCTTCAGCACCTTC<br>AAGTGCTACGGCGTCTCCCCTACAAAGCTG<br>AATGACCTGTGCTTCACCAACGTGTATGCC<br>GACAGCTTCGTGATTAGAGGCGATGAGGTG<br>AGGCAGATCGCCCCTGGACAAACCGGCAAC<br>ATCGCCGATTATAACTACAAGCTGCCTGAC<br>GACTTCACCGGCTGCGTGATCGCCTGGAAC<br>AGCAACAACCTGGACAGCAAGGTCGGCGGC<br>AACTACAACTACCTCTACAGACTGTTCAGA<br>AAGTCCAACCTGAAGCCTTTCGAGAGGGAC<br>ATCAGCACCGAGATTTACCAAGCCGGCAGC<br>ACCCCTTGCAACGGCGTGAAGGGATTTAAC<br>TGCTATTTCCCTCTGCAGAGCTACGGCTTC<br>CAACCTACCTATGGAGTGGGCTACCAACCC<br>TACAGAGTGGTGGTCCTGAGCTTCGAACTG<br>CTGCACGCCCCTGCCACCGTGTGTGGCCCT<br>AAAAAGAGCACCAATCTCGTGAAAAACAAG<br>AGAGTGCAGCCTACAGAAAGCATTGTGAGA<br>TTTCCTAATATCACCAACCTGTGCCCTTTC<br>GGCGAGGTGTTCAACGCTACAAGATTCGCT<br>AGCGTGTACGCCTGGAATAGAAAGAGAATC<br>AGCAACTGCGTGGCCGACTACAGCGTGCTG<br>TACAACAGCGCTTCCTTTAGCACCTTCAAG<br>TGTTACGGCGTGAGCCCCACCAAGCTCAAC<br>GACCTGTGCTTCACAAACGTGTACGCTGAC<br>AGCTTCGTGATCAGAGGCGATGAGGTGAGA<br>CAGATCGCCCCTGGCCAAACCGGCAACATC<br>GCCGATTACAACTATAAGCTCCCTGATGAC<br>TTCACCGGCTGCGTGATCGCTTGGAACAGC<br>AACAACCTGGACAGCAAGGTGGGCGGCAAC<br>TACAACTACCTCTATAGACTGTTCAGAAAA<br>TCCAACCTGAAGCCTTTCGAGAGAGACATC<br>TCCACCGAGATTTATCAAGCCGGAAGCACC<br>CCCTGCAATGGCGTGAAGGGCTTCAACTGC<br>TACTTCCCTCTCCAATCCTACGGCTTCCAA<br>CCTACCTACGGAGTGGGCTATCAGCCCTAC<br>AGAGTGGTCGTGCTGAGCTTCGAGCTCCTG<br>CACGCCCCTGCCACCGTGTGCGGCCCTAAA<br>AAGAGCACCAACCTGGTCAAAAATAAGAGA<br>GTGCAGCCCACCGAGAGCATCGTGAGATTC<br>CCTAATATCACCAACCTGTGCCCTTTTGGA<br>GAGGTGTTCAACGCCACAAGATTCGCTAGC<br>GTGTACGCCTGGAATAGAAAGAGGATCAGC<br>AACTGCGTGGCCGACTACAGCGTGCTCTAC<br>AACAGCGCCTCCTTCAGCACCTTTAAGTGT<br>TACGGCGTCTCCCCTACCAAGCTGAACGAT<br>CTCTGCTTTACCAACGTGTACGCCGACAGC<br>TTTGTGATCAGAGGCGACGAAGTGAGGCAA<br>ATCGCTCCTGGACAGACCGGAAACATCGCC<br>GACTACAACTACAAGCTGCCTGACGACTTC<br>ACCGGCTGCGTCATCGCCTGGAATAGCAAC<br>AACCTGGATAGCAAAGTCGGAGGCAACTAC<br>AACTACCTGTACAGACTCTTCAGAAAGAGC<br>AACCTCAAACCTTTCGAGAGAGACATCAGC<br>ACAGAGATCTACCAAGCCGGCAGCACCCCT<br>TGCAACGGAGTCAAGGGCTTCAACTGCTAC<br>TTTCCTCTGCAGAGCTACGGCTTTCAGCCT<br>ACCTACGGCGTCGGCTATCAGCCTTACAGA<br>GTGGTCGTGCTCAGCTTCGAACTCCTGCAC |

-continued

SEQUENCE TABLE

| Number | Sequence |
|---|---|
| | GCCCCCGCCACCGTGTGCGGACCTAAAAAG<br>AGCACCAATCTGGTGAAGAACAAATGA |
| SEQ ID No. 18 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGKIADYNYKLPDDFTGCVIAWN<br>SNNLDSKVGGNYNYLYRLFRKSNLKPFERD<br>ISTEIYQAGSTPCNGVEGFNCYFPLQSYGF<br>QPTNGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGKIADYNYKLPDD<br>FTGCVIAWNSNNLDSKVGGNYNYLYRLFRK<br>SNLKPFERDISTEIYQAGSTPCNGVEGENC<br>YFPLQSYGFQPTNGVGYQPYRVVVLSFELL<br>HAPATVCGPKKSTNLVKNKRVQPTESIVRF<br>PNITNLCPFGEVFNATRFASVYAWNRKRIS<br>NCVADYSVLYNSASFSTFKCYGVSPTKLND<br>LCFTNVYADSFVIRGDEVRQIAPGQTGKIA<br>DYNYKLPDDFTGCVIAWNSNNLDSKVGGNY<br>NYLYRLFRKSNLKPFERDISTEIYQAGSTP<br>CNGVEGENCYFPLQSYGFQPTNGVGYQPYR<br>VVVLSFELLHAPATVCGPKKSTNLVKNK |
| SEQ ID No. 19 | MRVQPTESIVRFPNITNLCPFGEVFNATRF<br>ASVYAWNRKRISNCVADYSVLYNSASFSTF<br>KCYGVSPTKLNDLCFTNVYADSFVIRGDEV<br>RQIAPGQTGKIADYNYKLPDDFTGCVIAWN<br>SNNLDSKVGGNYNYLYRLFRKSNLKPFERD<br>ISTEIYQAGSTPCNGVEGFNCYFPLQSYGF<br>QPTNGVGYQPYRVVVLSFELLHAPATVCGP<br>KKSTNLVKNKRVQPTESIVRFPNITNLCPF<br>GEVFNATRFASVYAWNRKRISNCVADYSVL<br>YNSASFSTFKCYGVSPTKLNDLCFTNVYAD<br>SFVIRGDEVRQIAPGQTGKIADYNYKLPDD<br>FTGCVIAWNSNNLDSKVGGNYNYLYRLFRK<br>SNLKPFERDISTEIYQAGSTPCNGVEGENC<br>YFPLQSYGFQPTNGVGYQPYRVVVLSFELL<br>HAPATVCGPKKSTNLVKNK |

DETAILED DESCRIPTION OF THE EMBODIMENTS

The present invention discloses a recombinant severe acute respiratory syndrome coronavirus 2 (SARS-CoV-2) RBD trimer protein vaccine capable of generating broad-spectrum cross neutralization activity, and a preparation method and use thereof. Those skilled in the art may make a proper improvement on process parameters for implementation with reference to the content of the specification. It should be particularly noted that all similar substitutes and modifications are apparent to one of skill in the art and are considered to be included within the present invention; and related persons can obviously make a modification or a proper change and combination on the content of this paper without departing from the content, the spirit and the scope of the present invention, so as to implement and apply the technology of the present invention.

In the present invention, unless otherwise specified, scientific and technical terms used herein have the meaning as commonly understood by those skilled in the art. Unless otherwise expressly stated, throughout the specification and claims, the term "including" or its variations such as "including" or "comprising" will be understood as including the stated elements or components, but not excluding other elements or components. Unless otherwise expressly stated, throughout the specification and claims, the term "RBD" represents an RBD structural domain of a spike protein of SARS-CoV-2, which may be understood to be interchangeably with "RBD" or "SARS-CoV-2 RBD region".

The following makes interpretation for some terms in the present invention.

The term "severe acute respiratory syndrome coronavirus 2", that is, SARS-CoV-2, belongs to a single-stranded positive strand RNA virus, SARS-like virus species, sarbecovirus subgenus, betacoronavirus, positive coronavirus, coronaviridae, nidovirales, with a cyst membrane. The full length of genome is about 29.9 kb. Most of the genome encodes non-structural proteins and participates in virus replication and translation functions; and a few sequences encode structural proteins, such as a spike protein (S protein), a membrane protein (M protein), a cyst membrane protein (E protein) and a nucleo protein (N protein). In addition, there are several accessory proteins: 3a, 3b, p6, 7a, 7b, 8b, 9b and orf14, and these proteins participate in viral assembly. S, M and E proteins constitute a virus cyst membrane, which is a main surface antigen of the virus causing immune response. The S protein is a transmembrane glycoprotein, has a molecular weight about 150 kDa, and forms a prominent homotrimer on the surface of the virus. The S protein consists of two functional subunits, and is cleaved at a boundary (an S1/S2 cleavage site) between the S1 subunit and the S2 subunit; and the two subunits keep non-covalent binding in conformation before fusion. The S2 subunit is composed of a plurality of structural domains, and has a main function of mediating the fusion between a virus and a host cell. The distal S1 subunit is structurally divided into four different structural domains: a N-terminal structural domain (NTD), a receptor binding structural domain (RBD), a C-terminal structural domain 1 (CTD1) and a C-terminal structural domain 2 (CTD2), where RBD is mainly responsible for binding with a receptor angiotensin converting enzyme 2 (ACE2) on the surface of the host cell, so that the virus is mediated to infect the host cell; therefore, the S protein and RBD are the main targets of the research and development of genetic engineering vaccine at present.

The term "trimer form" is a type in a higher structure of a protein. The protein including three protein subunits is in the trimer form.

The term "at least one" may be understood as that two of three amino acid sequences are the same or the three amino acid sequences are different.

The term "primary structure" is a linear sequence of an amino acid in a peptide or the protein. Conventionally, the primary structure of the protein refers to being from an amino terminal (N terminal) to a carboxy terminal (C terminal).

The term "fusion protein" refers to one, two or more expression products obtained by a DNA recombination technology after genetic recombination. A fusion protein technology is a targeted gene fusion and protein expression method performed for obtaining a great quantity of standard fusion proteins. A novel target protein with a plurality of functions may be constructed and expressed using the fusion protein technology.

The term "vector" is a nucleic acid vehicle, into which polynucleotide may be inserted. If the vector can make the protein, into which polynucleotide is inserted, be expressed, the vector is called an expression vector. The vector may be introduced into the host cell through transformation, transduction or transfection, so that genetic material elements carried by the vector can be expressed in the host cell. The vector is well known to those skilled in the art, including but not limited to: plasmids; phagemids; cosmids; artificial chromosomes, such as yeast artificial chromosome (YAC), bacterial artificial chromosome (BAC) or P1-derived artificial chromosome (PAC); phages such as lambda phages or M13 phages; and animal viruses. Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may include a variety of elements that control expression, including, but not limited to promoter sequences, transcription initiation sequences, enhancer sequences, selection elements, and reporter genes. In addition, the vector may further include a replication start site.

The term “host cell” is a cell, into which the nucleic acid molecule has been introduced through a molecular biological technology. These technologies include transfection of the viral vector, transformation with the plasmid vector, and introduction of naked DNA through electroporation, lipofection and particle gun acceleration.

The term “treatment” refers to that the possibility of disease pathologies and occurrence of disease symptoms are reduced, so that, for example, a subject has a longer survival time or reduced discomfort to a certain degree. Treatment may refer to the ability of a therapy reducing the disease symptoms, signs or causes if a therapy is given to the subject. Treatment further refers to relieving or reducing at least on clinical symptom, and/or inhibiting or delaying a progress of a symptom, and/or preventing or delaying the onset of a disease or a condition.

The term “subject” refers to any person or other animals, particularly, other mammals, receiving prevention, treatment and diagnosis. Other mammals may include, for example, a dog, a cat, cattle, horse, sheep, pig, a goat, a rabbit, a rat, a guinea pig, a mouse and the like.

To make those skilled in the art better understand the technical solutions of the present invention, the present invention will be further described in detail below in combination with the specific examples.

Example 1: Design of SARS-CoV-2 RBD Trimer Protein Based on Protein Structure and Computational Biology Through comparison and analysis of an SARS-CoV-2 representative mutant strain and a prototype strain (as shown in Table 1), amino acid mutations occurred in a Beta (B.1.351) mutant strain at three sites, that is, K417N, E484K and N501Y; and amino acid mutations occurred in a Kappa (B.1.617.1) mutant strain at two sites, that is, L452R and E484Q. E484K is considered as the most important site mutation leading to immune scape. Through molecular dynamic simulation and free energy calculation, it is found that E484K mutation will significantly reduce the affinity of an RBD and a plurality of neutralizing monoclonal antibodies. In 10 mutant strains that are classified as VOC and VOI and listed by WHO, 6 mutant strains include the E484K mutation. In addition, L452R mutation has been proved to escape the neutralizing antibody and the serum of a recovered COVID-19 patent, and in the ten VOC and VOI mutant strains, three strains include the L452R mutation. Experimental evidence shows that K417N and N501Y mutations can resist some neutralizing antibodies, and in the ten VOC and VOI mutant strains, four strains include the N501Y mutation. In addition, through the evolutionary analysis of 1.2 million known SARS-CoV-2 sequences, it is found that E484K, L452R and N501Y are the most important convergent evolutionary mutation in the RBD. These mutations appear independently in numerous different virus lineages, indicating that these mutations have obvious selection advantages in virus evolution and predicting that these mutations may appear independently or in combination in the future mutant strains. Therefore, it is of great significance to research and develop a COVID-19 vaccine with a broad-spectrum protection ability across epidemic strains.

Through analysis on the spatial structure (as shown in FIG. 1) of a natural S protein trimer and calculation on a spatial distance between an N terminal and a C terminal of the RBD structural domain, it is found that trimerization can be realized by the structural feature of the RBD without introducing an exogenous vector or sequence, and a larger spatial barrier is not present. Based on this, SARS-CoV-2 S protein RBD region sequence fragments (the 319th to 537th amino acids) of different mutant strains are intercepted, and the three RBD region fragments are connected end to end in series to form a new fusion protein. The sequences of SARS-CoV-2 prototype strain S protein RBD region fragments (the 319th to 537th amino acids) are shown in SEQ ID NO.1, the sequences of the S protein RBD region fragments (the 319th to 537th amino acids) of the Beta (B.1.351) mutant strain are shown in SEQ ID NO.2, and the sequences of the S protein RBD region fragments (the 319th to 537th amino acids) of the Kappa (B.1.617.1) mutant strain are shown in SEQ ID NO.3.

Through different combinations of SEQ ID NO.1, SEQ ID NO.2 and SEQ ID NO.3, a trimer protein can simultaneously generate the cross neutralizing activity of different SARS-CoV-2 strains to achieve the purpose of researching and developing a broad-spectrum vaccine, which is specifically as follows: a trimer protein A formed by sequentially connecting, SEQ ID NO.1, SEQ ID NO.2 and SEQ ID NO.3, with the amino acid sequence shown in SEQ ID NO.4; a trimer protein B formed by sequentially connecting, SEQ ID NO.1, SEQ ID NO.2 and SEQ ID NO.1, with the amino acid sequence shown in SEQ ID NO.5; a trimer protein C formed by sequentially connecting, SEQ ID NO.1, SEQ ID NO.2 and SEQ ID NO.2, with the amino acid sequence shown in SEQ ID NO.6; a trimer protein D formed by sequentially connecting, SEQ ID NO.2, SEQ ID NO.1 and SEQ ID NO.2, with the amino acid sequence shown in SEQ ID NO.7; and a trimer protein E formed by sequentially connecting, SEQ ID NO.2, SEQ ID NO.2 and SEQ ID NO.2, with the amino acid sequence shown in SEQ ID NO.8.

Figure 2:
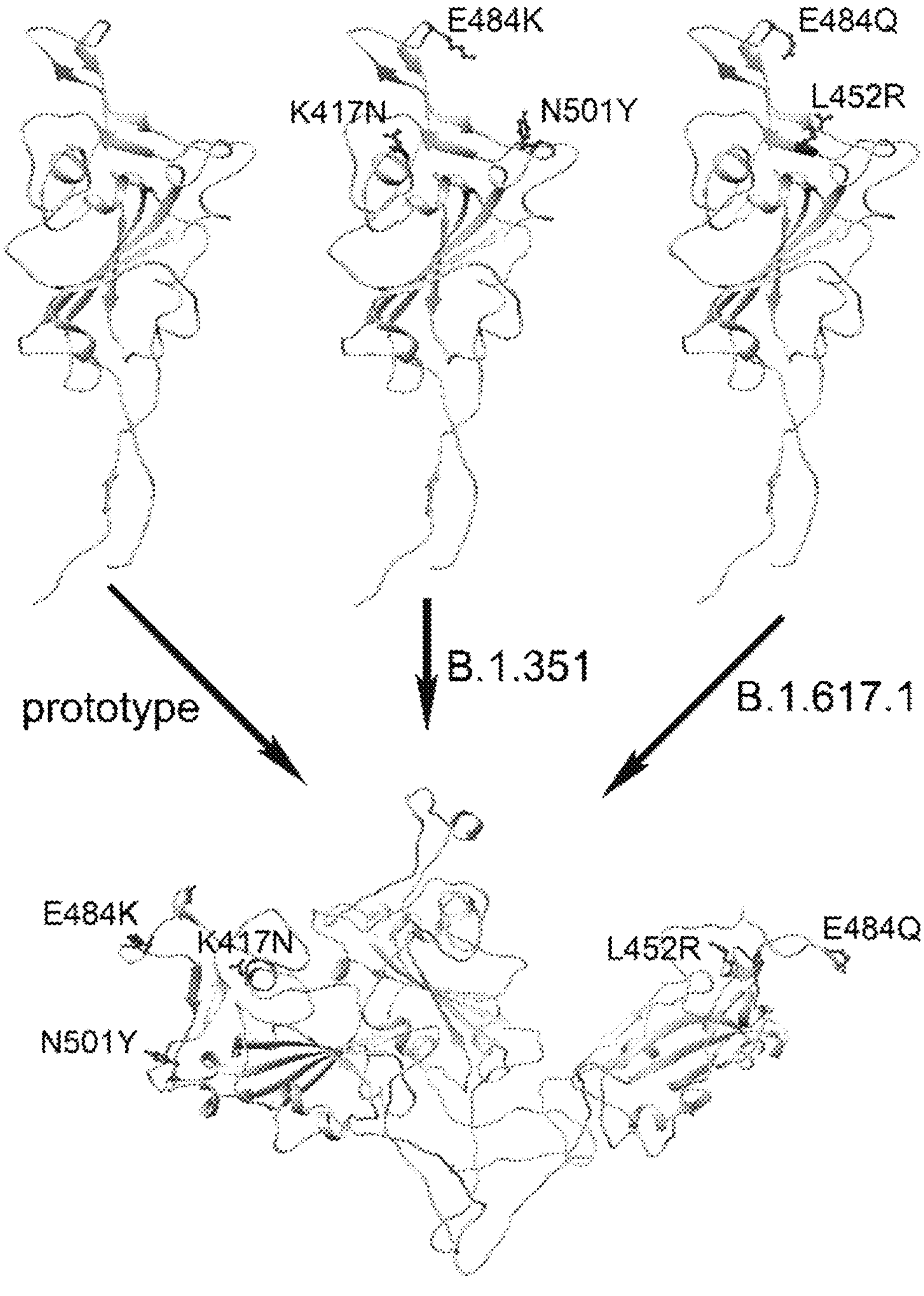
FIG. 2 is a homologous modeling result diagram of a trimer protein A according to Example 1 of the present invention.

Taking the trimer protein A (with the amino acid sequence shown in SEQ ID NO.4) as an example, a possible spatial structure is constructed by homologous modeling. The result is shown in FIG. 2 and shows that the fusion protein includes three independent RBD structural domains, a trimer form with stable antigen conformation may be formed, and the protein covers a key active mutation site and a potential immune escape site. It is theoretically speculated that the recombinant vaccine taking the sites as target antigen has the broad-spectrum protection ability across epidemic strains. In addition, compared with the traditional strategy of preparing a plurality of monovalent vaccines to realize the broad-spectrum protection through multivalent protection, multivalent broad-spectrum protective effect is achieved on an antigen molecule, and the advantages in the time cost, economic cost and vaccine productivity of vaccine preparation are significant.

TABLE 1

| Mutation of SARS-CoV-2 Representative Epidemic Strain RBD Region | | | | |
|---|---|---|---|---|
| WHO Name | Mutant Strain Lineage | VOC/ VOI | Discovery Time | Mutation of RBD Region |
| Alpha | B.1.1.7 | VOC | September 2020 | N501Y |
| Beta | B.1.351 | VOC | May 2020 | K417N, E484K, N501Y |
| Gamma | P.1 | VOC | November 2020 | K417T, E484K, N501Y |
| Delta | B.1.617.2 | VOC | November 2020 | L452R, T478K |
| Epsilon | B.1.427/B.1.429 | VOI | March 2020 | L452R |
| Zeta | P.2 | VOI | April 2020 | E484K |
| Eta | B.1.525 | VOI | December 2020 | E484K |
| Theta | P.3 | VOI | January 2021 | E484K, N501Y |
| Iota | B.1.526 | VOI | November 2020 | E484K |
| Kappa | B.1.617.1 | VOI | October 2020 | L452R, E484Q |

Example 2: Expression, Purification and Identification of Trimer Protein

According to codon preference of a CHO cell expression system, codon optimization was performed on a nucleotide sequence encoding a protein A to a protein E (with amino acid sequences shown in SEQ ID NO.4 to SEQ ID NO.8). The optimized nucleotide sequence of the protein A (with the amino acid sequence shown in SEQ ID NO.4) is shown in SEQ ID NO.9, the optimized nucleotide sequence of the protein B (with the amino acid sequence shown in SEQ ID NO.5) is shown in SEQ ID NO.10, the optimized nucleotide sequence of the protein C (with the amino acid sequence shown in SEQ ID NO.6) is shown in SEQ ID NO.11, SEQ ID NO.12, SEQ ID NO.13 or SEQ ID NO.14, the optimized nucleotide sequence of the protein D (with the amino acid sequence shown in SEQ ID NO.7) is shown in SEQ ID NO.15, and the optimized nucleotide sequence of the protein E (with the amino acid sequence shown in SEQ ID NO.8) is shown in SEQ ID NO.16 or SEQ ID NO.17.

Figure 3:
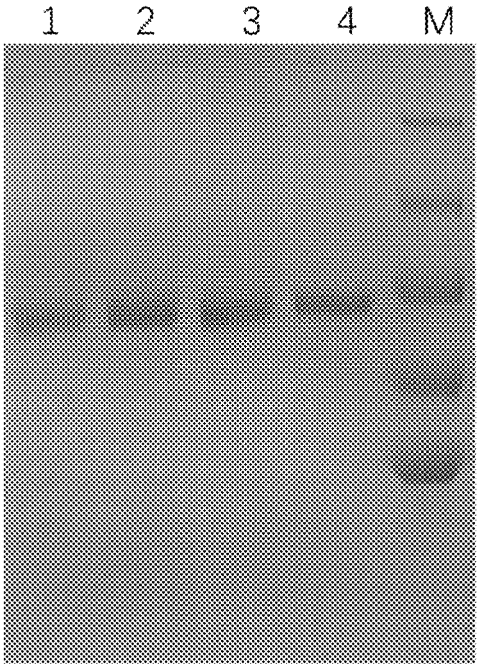
FIG. 3 is an SDS-PAGE detection result according to Example 2 of the present invention, where a lane 1 is a trimer protein, a lane 2 is a trimer protein A, a lane 3 is a trimer protein B, a lane 4 is a trimer protein C, and M is a protein marker (with a molecular weight standard being kDa: 250, 130, 100, 70, 55, 35, 25, 15 and 10)

After being constructed, a CHO cell expression vector was transfected into a 293FT cell or a CHO cell to construct a recombinant cell line. A cell line capable of stably secreting and expressing the RBD trimer protein was screened by a limited dilution method. Finally, the protein A, the protein B and the protein C were expressed successfully. Through a series of chromatographic purification, the protein A, the protein B and the protein C obtain trimer proteins with the purity greater than or equal to 95%. The expression quantities of the protein D and the protein E are excessively low, and the target protein with higher purity is not obtained after purification. The SDS-PAGE detection result of the protein A, the protein B and the protein C is shown in FIG. 3. The molecular weight of the protein is 70 to 100 kD; and some substances, such as a dimer protein and a monomer protein, related to the product is visible.

Figure 4:
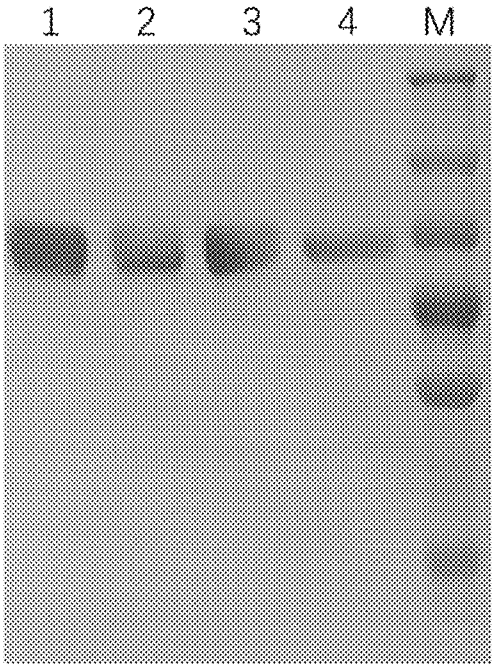
FIG. 4 is a Western-blot identification diagram of the trimer protein obtained through purification according to Example 2 of the present invention, where a lane 1 is a trimer protein, a lane 2 is a trimer protein A, a lane 3 is a trimer protein B, a lane 4 is a trimer protein C, and M is a protein marker (with a molecular weight standard being kDa: 250, 130, 100, 70, 55, 35, 25, 15 and 10)

The purified protein A, protein B and protein C were electrotransferred onto a polyvinylidene fluoride (PVDF) membrane after being subjected to SDS-PAGE electrophoresis, and then were subjected to Western-blot identification using an RBD-specific antibody (manufacturer: Beijing Sino Biological Ltd. Co.; article number: 40591-T62; dilutability: 2000 folds) (the result is shown in FIG. 4). It shows that all the proteins may bind to the RBD-specific antibody, and has good biological activity. The purified protein A, protein B and protein C were subjected to molecular-exclusion chromatography analysis by a TSKgel G2500PW gel chromatographic column, and the purity of all the purified proteins is greater than 90%.

Example 3: Biological Analysis on Binding of Neutralizing Monoclonal Antibody The purified trimer protein A, protein B and protein C, a trimer protein (obtained by performing 293FT cell or CHO cell recombinant expression and chromatographic purification on proteins, with the amino acid sequence shown in SEQ ID NO.18, which are formed by sequentially connecting three amino acid fragments shown in SEQ ID NO.1), a dimer protein (obtained by performing 293FT cell or CHO cell recombinant expression and chromatographic purification on proteins, with the amino acid sequence shown in SEQ ID NO.19, which are formed by sequentially connecting two amino acid fragments shown in SEQ ID NO.1), an RBD protein (manufacturer: Beijing Sino Biological Ltd. Co.; article number: 40592-V08B), an RBD protein (K417N, E484K and N501Y; manufacturer: Beijing Sino Biological Ltd. Co.; article number: 40592-V08H85) consistent with the virus mutation sites of Beta (B.1.351) strain, and an RBD protein (L452R and E484Q; manufacturer: Beijing Sino Biological Ltd. Co.; article number: 40592-V08H85) consistent with the virus mutation sites of Kappa (B.1.617.1) strain were diluted with coating liquid to 4 μg/ml, 2 μg/ml, 1 μg/ml, 0.5 μg/ml, 0.25 μg/ml, 0.125 μg/ml, 0.0625 μg/ml, 0.03125 μg/ml, 0.015625 μg/ml, 0.007813 μg/ml, 0.003906 μg/ml, 0.001953 μg/ml, and were coated to a 96-well ELISA plate by 100 μl/well at 4° C. for 8 to 12 h. and a blank well served as negative control; after the plate was washed with a PBST solution, a confining liquid was added for confining at 37° C. for 3 h; after the plate was washed by the PBST solution, a diluted MM43 monoclonal antibody (manufacturer: Beijing Sino Biological Ltd. Co.; article number: 40591-MM43; dilutability: 2000 folds) or a diluted MM57 monoclonal antibody (manufacturer: Beijing Sino Biological Ltd. Co.; article number: 40592-MM57; dilutability: 2000 folds) or a diluted R001 monoclonal antibody (manufacturer: Beijing Sino Biological Ltd. Co.; article number: 40592-R001; dilutability: 2000 folds) or a diluted R117 monoclonal antibody (manufacturer: Beijing Sino Biological Ltd. Co.; article number: 40592-R117; dilutability: 2000 folds) were respectively added in 100 μl/well for incubation at 37° C. for 1 h; after the plate was washed with the PBST solution, a diluted horse radish peroxidase-labeled goat anti-mouse or goat anti-rabbit antibody was added in 100 μl/well for incubation at 37° C. for 1 h; after the plate was washed with the PBST solution, chromogenic solutions A and B were added sequentially for developing for 5 to 10 min at room temperature, and a stop solution C was added; and values were read from a microplate reader at double wavelengths (OD450 nm and 630 nm) to determine a cutoff value, and a curve of protein concentration-absorbance value was drawn.

Figure 5:
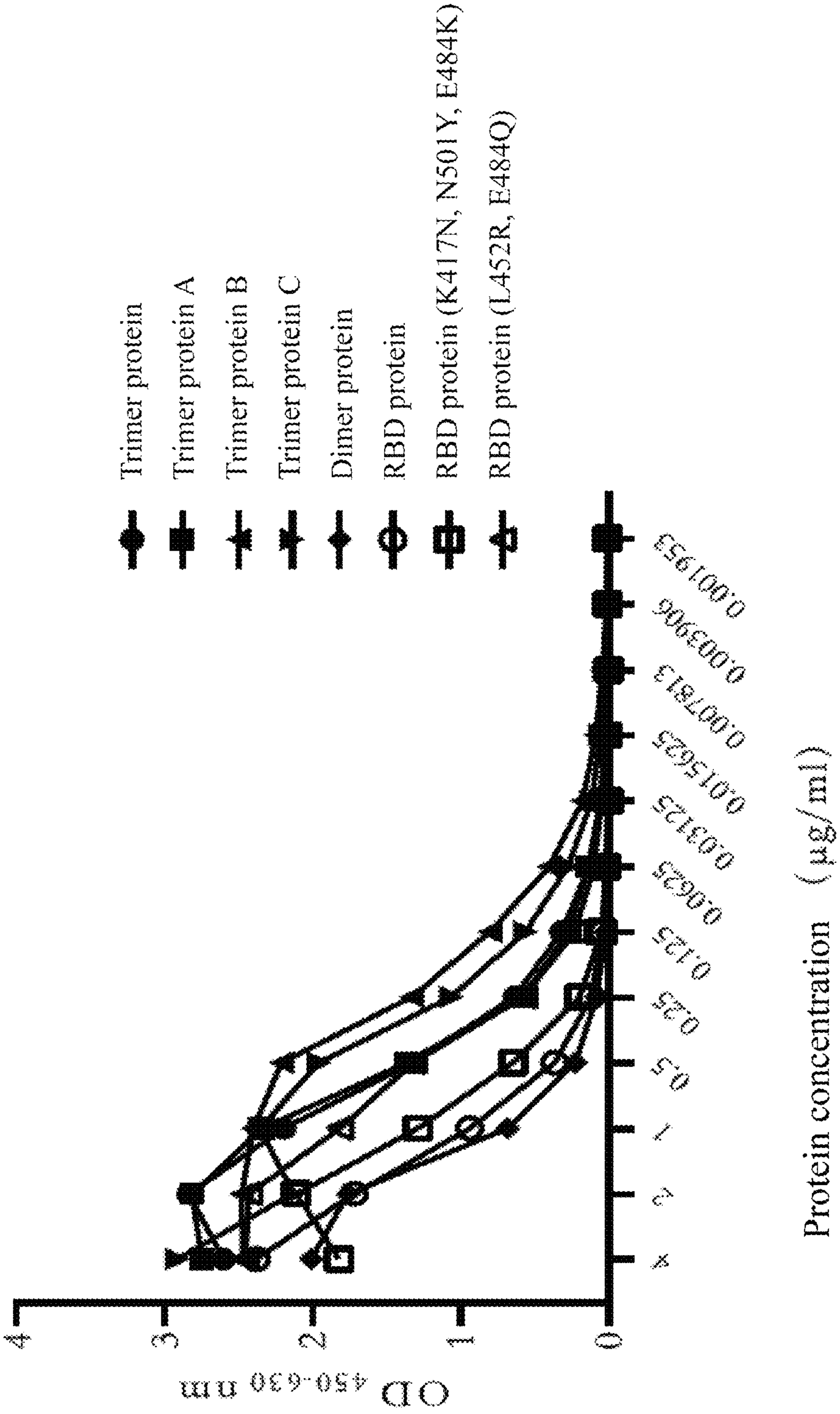
FIG. 5 is a binding curve diagram of a recombinant expressed protein in Example 3 of the present invention and an MM43 neutralizing monoclonal antibody.
Figure 6:
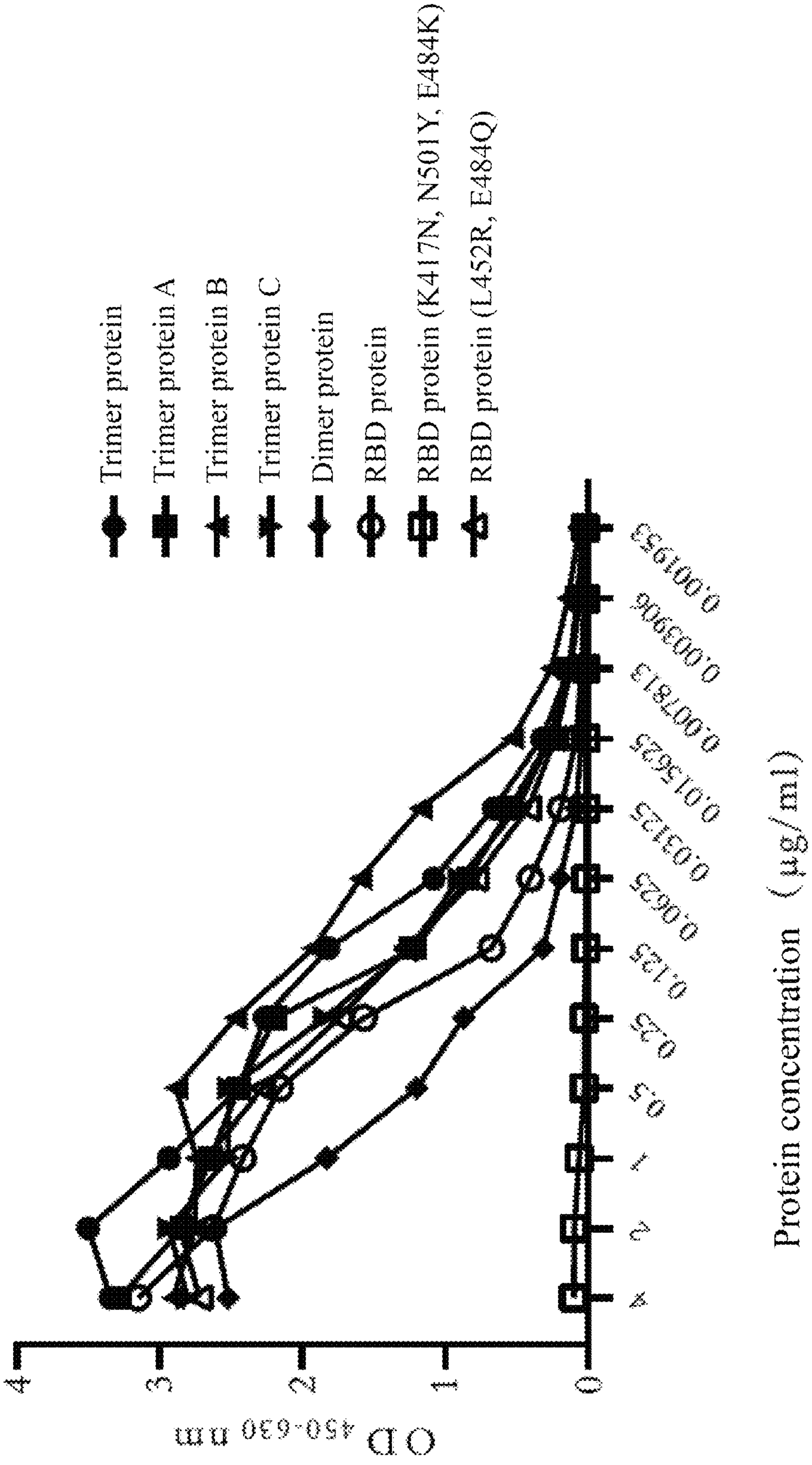
FIG. 6 is a binding curve diagram of a recombinant expressed protein in Example 3 of the present invention and an MM57 neutralizing monoclonal antibody.
Figure 7:
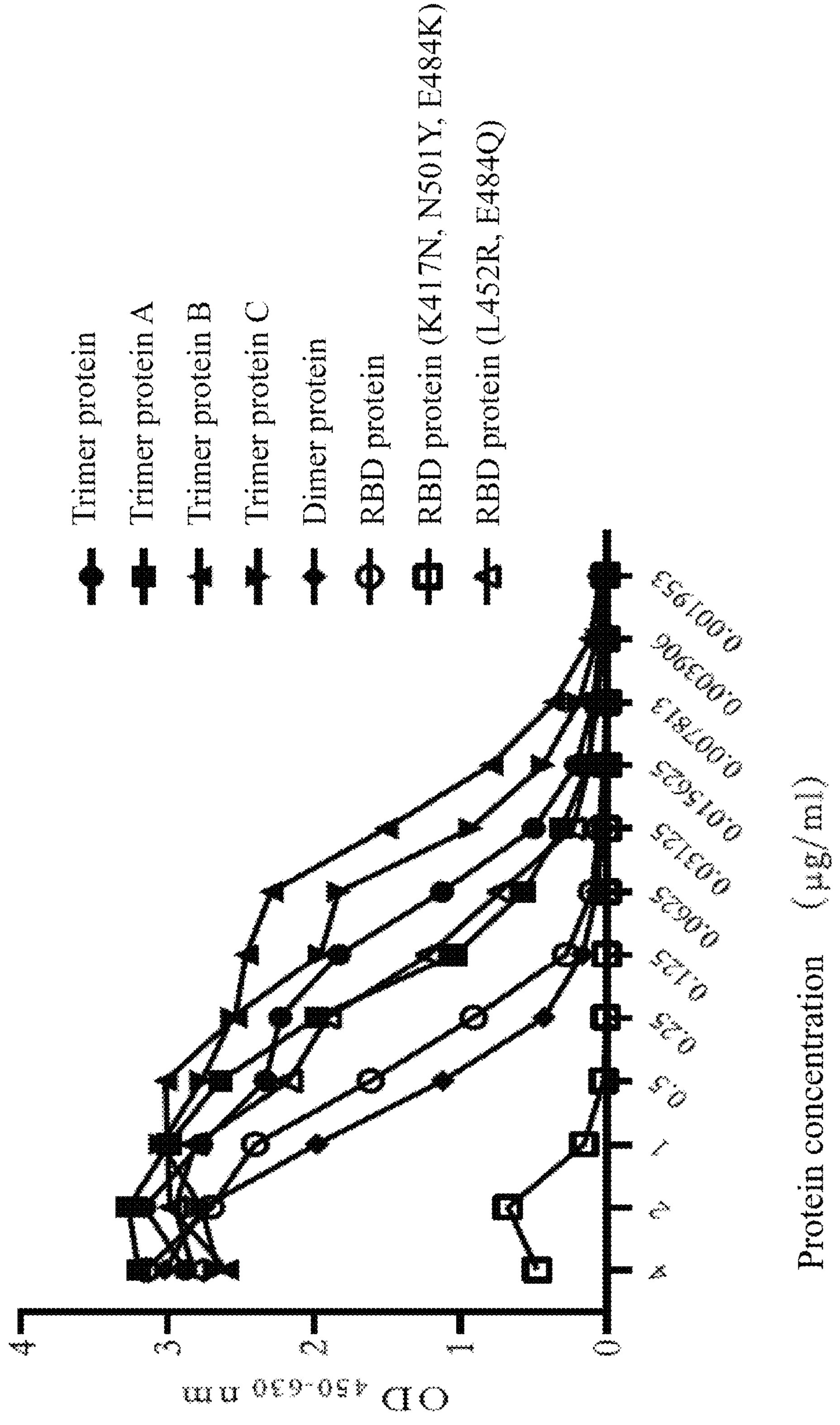
FIG. 7 is a binding curve diagram of a recombinant expressed protein in Example 3 of the present invention and an R001 neutralizing monoclonal antibody.
Figure 8:
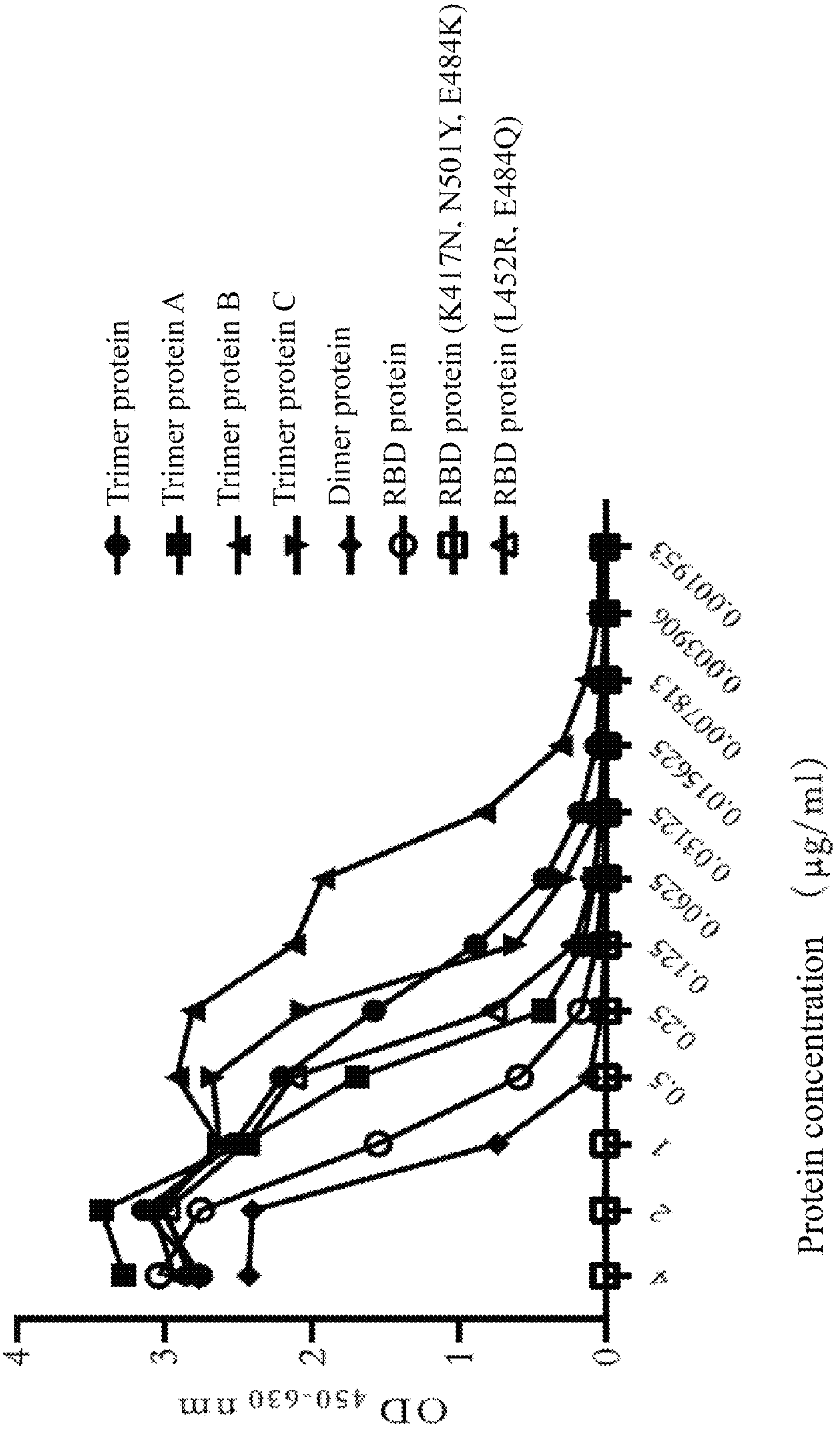
FIG. 8 is a binding curve diagram of a recombinant expressed protein in Example 3 of the present invention and an R117 neutralizing monoclonal antibody.

The result of the binding activity with the MM43 monoclonal antibody is shown in FIG. 5, the result of the binding activity with the MM57 monoclonal antibody is shown in FIG. 6, the result of the binding activity with the R001 monoclonal antibody is shown in FIG. 7, and the result of the binding activity with the R117 monoclonal antibody is shown in FIG. 8. It can be seen from the results that the trimer protein A is bound to all the neutralizing monoclonal antibodies to varying degrees, where the binding activity with the MM43 antibody is basically consistent with the trimer protein, and the binding activity of the MM57 and R117 monoclonal antibodies is lower than the trimer protein, indicating that the trimer protein has the RBD protein property of the prototype strain, and also has the RBD protein characteristic of the Beta (B.1.351) strain.

Figure 9:
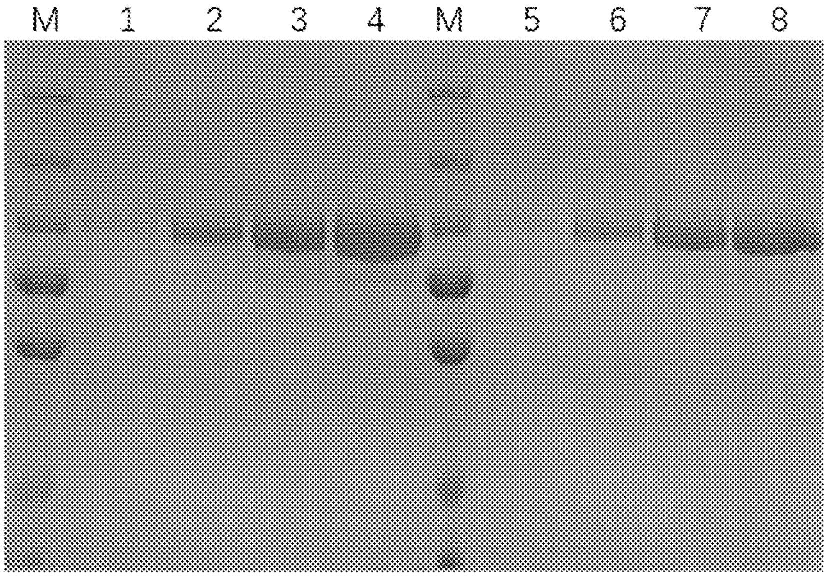
FIG. 9 is an SDS-PAGE detection result diagram of a trimer protein A in Example 4 of the present invention, where a lane 1 to a lane 4 are trimer proteins with different protein concentrations, a lane 5 to a lane 8 are trimer proteins A with different protein concentrations, and M is a protein marker (with a molecular weight standard being kDa: 250, 130, 100, 70, 55, 35, 25, 15 and 10)
Figure 10:
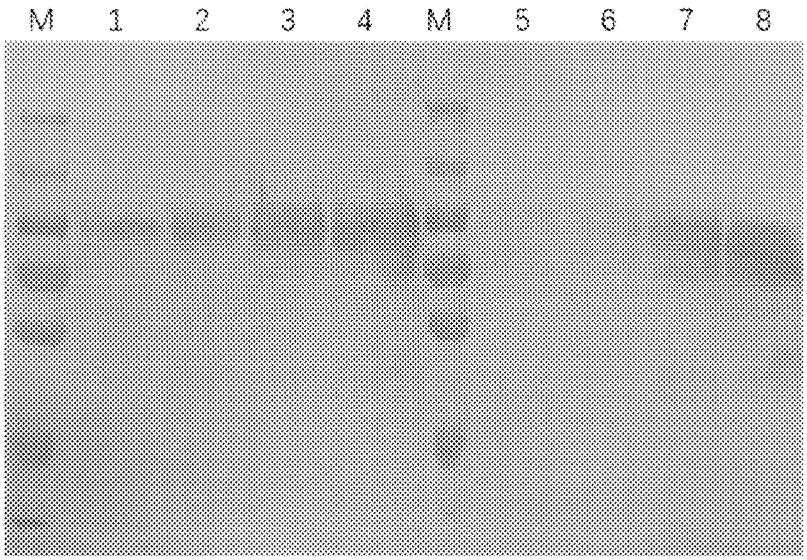
FIG. 10 is a Western-blot detection result diagram of a trimer protein A in Example 4 of the present invention, where a lane 1 to a lane 4 are trimer proteins with different protein concentrations, a lane 5 to a lane 8 are trimer proteins A with different protein concentrations, and M is a protein marker (with a molecular weight standard being kDa: 250, 130, 100, 70, 55, 35, 25, 15 and 10)
Figure 11:
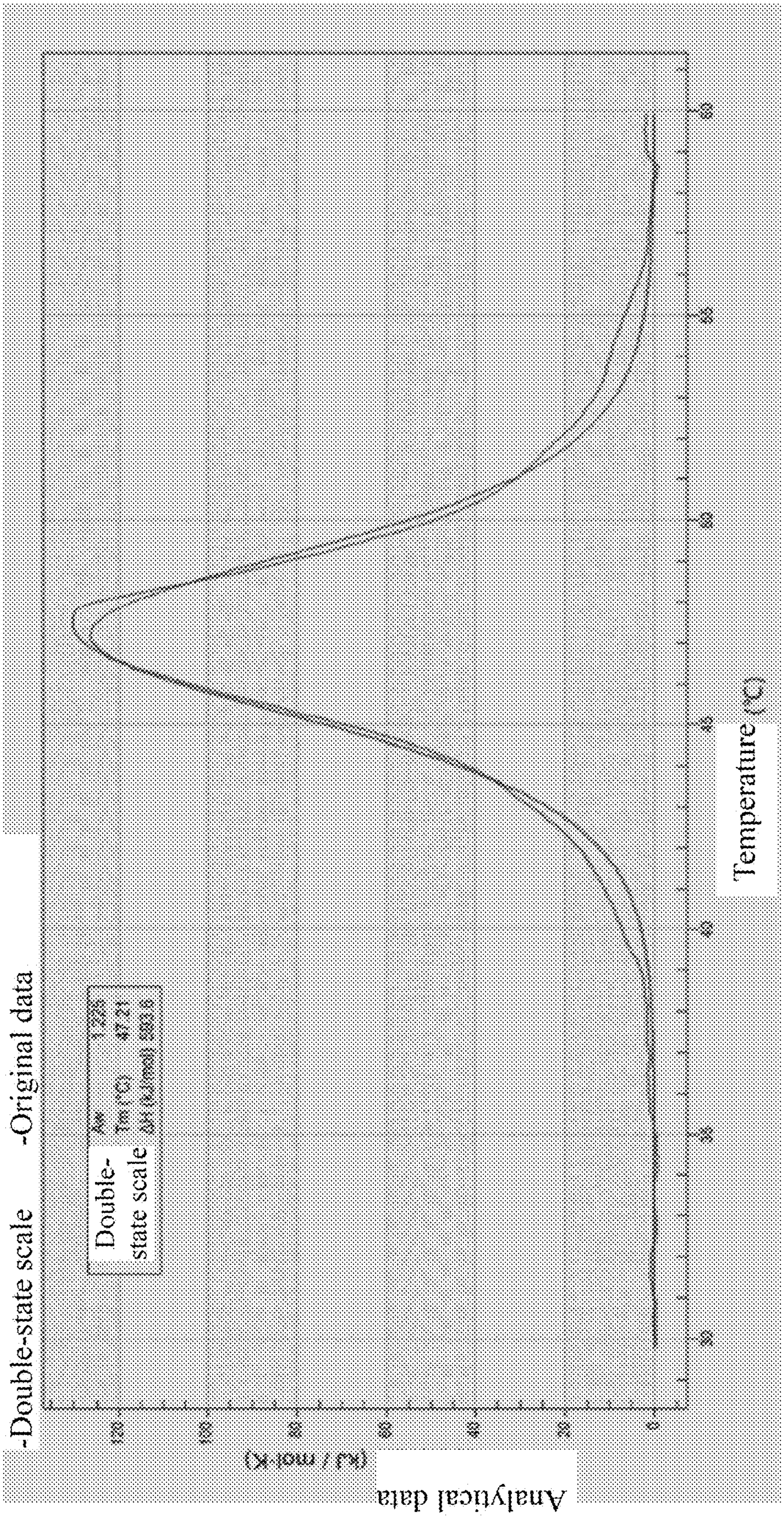
FIG. 11 is a heat stability result diagram of detecting a trimer protein A using a calorimetric differential scanning technology according to Example 4 of the present invention.
Figure 12:
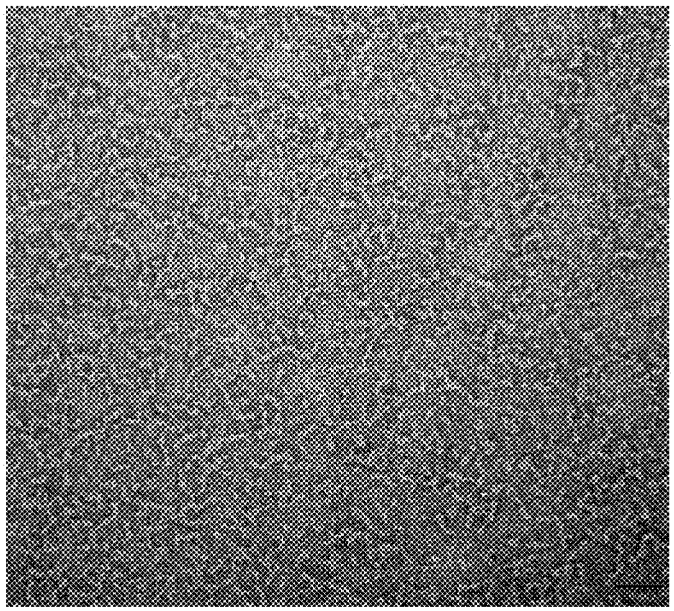
FIG. 12 is a result diagram of observing the form of a trimer protein A by a transmission electron microscope according to Example 4 of the present invention.
Figure 13:
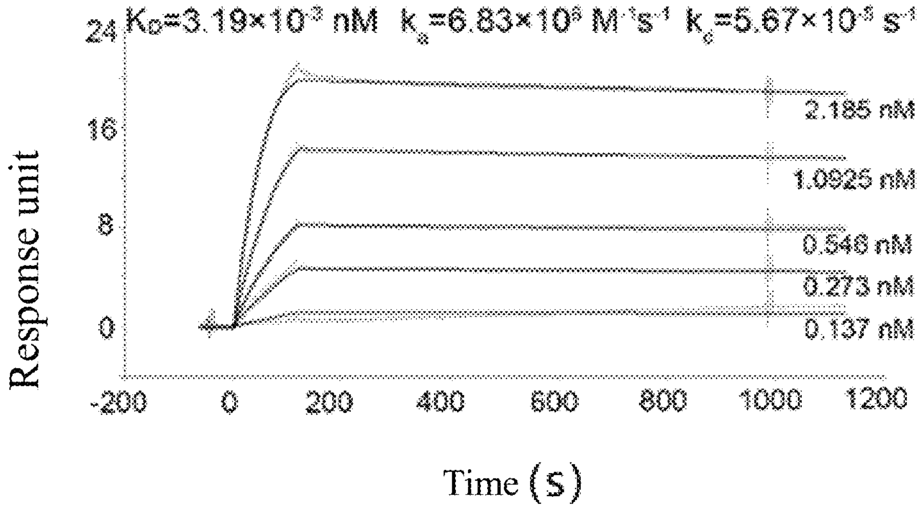
FIG. 13 is a result diagram of detecting the affinity of a trimer protein A and an hACE2 receptor using surface plasmon resonance technology according to Example 4 of the present invention.

Example 4: Physical and Chemical Properties and Activity Detection of Trimer Protein A A primary sequence of a trimer protein A includes RBD region amino acid sequences of a prototype strain, a Beta (B.1.351) mutant strain and a Kappa (B.1.617.1) mutant strain, and is a mutations-integrated trimeric form of RBD (mutI tri-RBD). The purified trimer protein A was further analyzed. The results are shown in FIG. 9 and FIG. 10 through SDS-PAGE detection and Western-blot analysis and by taking the trimer protein as control. It can be seen that the molecular weight of the trimer protein A is basically the same as that of the trimer protein and between 70 and 100 kD. The integrated molecular weight of the protein is detected by an MALDI-TOF MS method. The molecular weight of the trimer protein A is about 87.836 kD and is slightly greater than a theoretical value (74 kD), which is related to protein glycosylation modification. The protein glycosylation modification is detected by an UPLC-MS method. The result shows that the recombinant expressed trimer protein A has glycosylation modification with many sites. The trimer protein A was subjected to secondary structure detection by a circular dichroism spectrum. The result shows that the α spiral ratio is 13.5%, the β folding ratio is 23.3%, the β corner ratio is 11.4%, and the other is 51.8%, which keeps basically consistent with the theoretical value. The formation of a disulfide bond was detected by an UPLC-MS method. The result also shows that each RBD monomer in the trimer protein A can form four pairs of disulfide bonds, which is consistent with the pairing result of the disulfide bonds in the RBD natural structure. The heat stability of the trimer protein A was detected by a differential scanning calorimetry The result is shown in FIG. 11. Tm value is 47.2° C., and the trimer protein A has high heat stability. The form of the protein was observed by a transmission electron microscope. The result is shown in FIG. 12. It can be seen that the grain diameter of the trimer protein A is small and about 3 to 5 nm, but a clearer morphological structure image is not observed. In addition, the affinity of the trimer protein A and the hACE receptor protein was detected by a surface plasmon resonance technology. The result is shown in FIG. 13. KD value is 3.19×10−3 nM through calculation. The trimer protein A and the hACE receptor protein have high affinity, which proves that the trimer protein A has high biological activity.

Example 5: Preparation of Recombinant SARS-CoV-2 Vaccine

The purified protein was diluted to twice a target antigen concentration and was mixed with an aluminium hydroxide adjuvant of 1.2 mg/ml in a ratio of 1:1 (w/w) for adsorption; a mixture was stirred by a magnetic stirrer for 40-120 min at a rotating speed of 200-300 rpm to obtain a semi-finished vaccine, where the content of a residual protein in a supernatant should be less than 10% of a total protein content; and the semi-finished vaccine was aseptically dispensed into vials by 0.5 ml per vial, so as to obtain finished vaccines.

Example 6: Evaluation on Immunological Effect of Recombinant SARS-CoV-2 Vaccine

Figure 14:
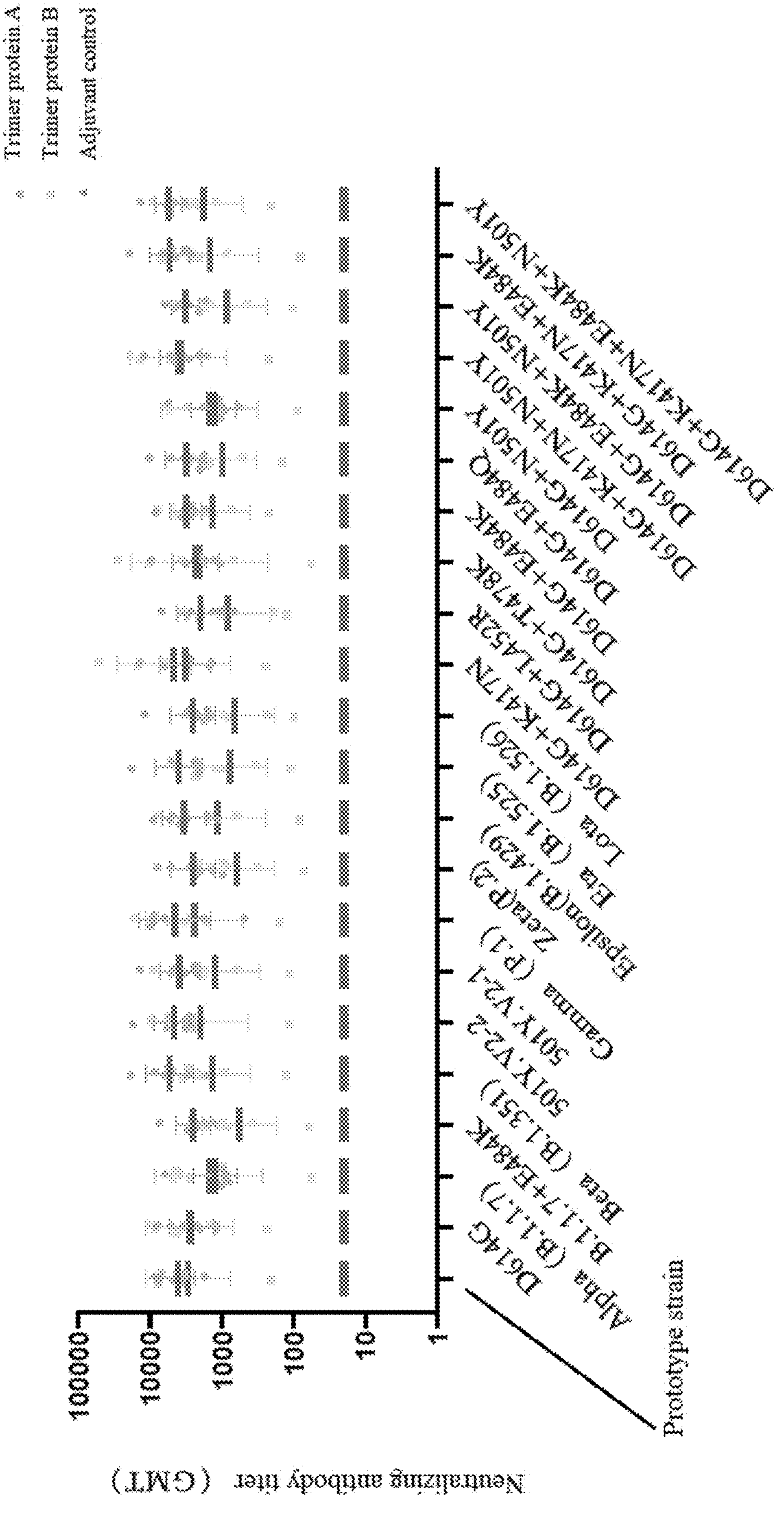
FIG. 14 is a result diagram of detecting the neutralizing antibody titer of mouse immune serum using a pseudovirus trace neutralization test according to Example 6 of the present invention.

The prepared vaccines (such as the trimer protein A or trimer protein) were respectively intraperitoneally injected for immunizing BALB/c mice (purchased from Beijing Vitalriver Experimental Animal Technology Ltd. Co., SPF grade, female, 6 to 8 weeks old), 2 μg/dose/mouse, respectively immunizing two needles at 0 w and 3 w, sampling blood at 5 w, and separating serum. The neutralizing activity of the immunized mouse serum for various pseudoviruses (as shown in Table 2) was detected by a pseudovirus trace neutralization test. The result is shown in FIG. 14, and the serum antibody GMT value is shown in Table 3. It can be seen that the trimer protein A can generate the neutralizing activity for various pseudoviruses, has a certain protection potential for the mutant strains causing immune escape and the mutant strains that may appear in the future, and is expected to generate a broad-spectrum protection ability.

TABLE 2

SARS-CoV-2 Pseudovirus Information List

| Number | Pseudovirus Name | Mutation of RBD Region Site |
|---|---|---|
| 1 | Prototype strain | None |
| 2 | D614G | None |
| 3 | Alpha (B.1.1.7) | N501Y |
| 4 | B.1.1.7 + E484K | N501Y, E484K |
| 5 | Beta (B.1.351) | K417N, E484K, N501Y |
| 6 | 501Y.V2-2 | N501Y |
| 7 | 501Y.V2-1 | N501Y |
| 8 | Gamma (P.1) | K417T, E484K, N501Y |
| 9 | Zeta (P.2) | E484K |
| 10 | Epsilon (B.1.429) | L452R |
| 11 | Eta (B.1.525) | E484K |
| 12 | Lota (B.1.526) | E484K |
| 13 | D614G + K417N | K417N |
| 14 | D614G + L452R | L452R |
| 15 | D614G + T478K | T478K |
| 16 | D614G + E484K | E484K |
| 17 | D614G + E484Q | E484Q |
| 18 | D614G + N501Y | N501Y |
| 19 | D614G + K417N + N501Y | K417N, N501Y |
| 20 | D614G + E484K + N501Y | E484K, N501Y |
| 21 | D614G + K417N + E484K | K417N, E484K |
| 22 | D614G + K417N + E484K + N501Y | K417N, E484K, N501Y |

TABLE 3

Neutralizing Antibody GMT Value (Pseudovirus Trace Neutralization Test)

| | | Neutralizing Antibody GMT Value | |
|---|---|---|---|
| Number | Pseudovirus Name | Trimer protein A | Trimer protein |
| 1 | Prototype strain | 4152 | 2970 |
| 2 | D614G | 2680 | 2851 |
| 3 | Alpha (B.1.1.7) | 1246 | 1532 |
| 4 | B.1.1.7 + E484K | 2533 | 569 |
| 5 | Beta (B.1.351) | 5377 | 1369 |
| 6 | 501Y.V2-2 | 4627 | 1980 |
| 7 | 501Y.V2-1 | 3911 | 1259 |
| 8 | Gamma (P.1) | 4546 | 2451 |
| 9 | Zeta (P.2) | 2548 | 622 |
| 10 | Epsilon (B.1.429) | 3388 | 1157 |
| 11 | Eta (B.1.525) | 4006 | 764 |
| 12 | Lota (B.1.526) | 2585 | 666 |
| 13 | D614G + K417N | 3299 | 4715 |
| 14 | D614G + L452R | 1982 | 832 |

TABLE 3-continued

Neutralizing Antibody GMT Value (Pseudovirus Trace Neutralization Test)

| Number | Pseudovirus Name | Neutralizing Antibody GMT Value Trimer protein A | Trimer protein |
|---|---|---|---|
| 15 | D614G + T478K | 2340 | 2074 |
| 16 | D614G + E484K | 3188 | 1368 |
| 17 | D614G + E484Q | 3176 | 984 |
| 18 | D614G + N501Y | 1303 | 1506 |
| 19 | D614G + K417N + N501Y | 3726 | 4092 |
| 20 | D614G + E484K + N501Y | 3233 | 872 |
| 21 | D614G + K417N + E484K | 5382 | 1468 |
| 22 | D614G + K417N + E484K + N501Y | 5616 | 1803 |

A pseudovirus trace neutralization test: the neutralizing antibody titer of the immunized serum for various pseudoviruses (as shown in Table 2) was detected by the pseudovirus trace neutralization test, the pseudovirus reporter gene was firefly luciferase, the pseudovirus working concentration is (1-2)×104 TCID50/ml, and the dilution ratio of the serum at 50% infection inhibition rate was calculated by a Reed-Muench method, that is the neutralizing antibody titer of the serum sample.

The above are preferred embodiments of the present invention, and it should be noted that, for those of ordinary skill in the art, several improvements and modifications may be made without departing from the principle of the present invention, and the improvements and modifications are also regarded to be within the protection scope of the present invention.

What is claimed is:

1. A recombinant Severe Acute Respiratory Syndrome (SARS)-Coronavirus (CoV)-2 receptor binding domain (RBD) trimer protein capable of generating broad-spectrum cross neutralization activity, wherein the trimer protein is composed of subunits of three SARS-COV-2 protein RBD regions, and the amino acid sequence of the trimer protein is the amino acid sequence shown in SEQ ID NO: 4.

2. A fusion protein, wherein the amino acid sequence of the fusion protein comprises the amino acid sequence of the recombinant SARS-COV-2 RBD trimer protein according to claim 1.

3. The fusion protein according to claim 2, further comprising one or more of signal peptides, tags or immune-enhancing peptides.

4. A nucleic acid molecule, comprising a nucleotide sequence encoding the recombinant SARS-COV-2 RBD trimer protein according to claim 1.

5. The nucleic acid molecule according to claim 4, wherein the nucleotide sequence of the nucleic acid molecule is the nucleotide sequence shown in SEQ ID NO: 9.

6. A vector, comprising the nucleic acid molecule according to claim 4.

7. An isolated host cell, comprising the nucleic acid molecule according to claim 4.

8. An isolated host cell, comprising the vector according to claim 6.

9. The isolated host cell according to claim 8, wherein the isolated host cell is *Escherichia coli*, a yeast cell, an insect cell or a mammalian cell.

10. The isolated host cell according to claim 9, wherein the isolated host cell is a Chinese Hamster Ovarian (CHO) cell.

11. A method for preparing the recombinant SARS-COV-2 RBD trimer protein according to claim 1, comprising the following steps:

step A): preparing a nucleic acid molecule comprising a nucleotide sequence encoding the recombinant SARS-COV-2 RBD trimer protein according to claim 1, constructing an expression vector of the nucleic acid molecule, and transforming or transfecting the expression vector into the isolated host cell according to claim 9;

step B): performing protein expression by using the isolated host cell of step A to obtain a protein expression product; and step C): purifying the protein expression product obtained in step B to obtain the recombinant SARS-COV-2 RBD trimer protein.

12. A recombinant protein vaccine, comprising the recombinant SARS-COV-2 RBD trimer protein according to claim 1, and an adjuvant.

13. The recombinant protein vaccine according to claim 12, wherein the adjuvant is aluminium hydroxide, aluminium phosphate, a generic oil-in-water adjuvant or CpG.

14. The recombinant protein vaccine according to claim 13, wherein the adjuvant is aluminium hydroxide.

15. A method for preparing the recombinant protein vaccine according to claim 12, wherein the recombinant SARS-COV-2 RBD trimer protein obtained through purification and the adjuvant are mixed.

16. A genetic engineering vector vaccine, comprising the nucleic acid molecule according to claim 4.

17. A nucleic acid vaccine, comprising the nucleic acid molecule according to claim 4.

18. A drug composition, comprising the vaccine according to claim 12, and a pharmaceutically acceptable vector.

19. A drug composition, comprising the vaccine according to claim 16, and an additional pharmaceutically acceptable vector.

20. A drug composition, comprising the vaccine according to claim 17, and a pharmaceutically acceptable vector.

* * * * *

SEQUENCE LISTING

```
<160> NUMBER OF SEQ ID NOS: 19

<210> SEQ ID NO 1
<211> LENGTH: 219
<212> TYPE: PRT
<213> ORGANISM: SARS-CoV-2

<400> SEQUENCE: 1

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys
    210                 215


<210> SEQ ID NO 2
<211> LENGTH: 219
```

-continued

<212> TYPE: PRT
<213> ORGANISM: SARS-CoV-2

<400> SEQUENCE: 2

Arg Val Gln Pro Thr Glu Ser Ile Val Arg Phe Pro Asn Ile Thr Asn
1 5 10 15

Leu Cys Pro Phe Gly Glu Val Phe Asn Ala Thr Arg Phe Ala Ser Val
20 25 30

Tyr Ala Trp Asn Arg Lys Arg Ile Ser Asn Cys Val Ala Asp Tyr Ser
35 40 45

Val Leu Tyr Asn Ser Ala Ser Phe Ser Thr Phe Lys Cys Tyr Gly Val
50 55 60

Ser Pro Thr Lys Leu Asn Asp Leu Cys Phe Thr Asn Val Tyr Ala Asp
65 70 75 80

Ser Phe Val Ile Arg Gly Asp Glu Val Arg Gln Ile Ala Pro Gly Gln
85 90 95

Thr Gly Asn Ile Ala Asp Tyr Asn Tyr Lys Leu Pro Asp Asp Phe Thr
100 105 110

Gly Cys Val Ile Ala Trp Asn Ser Asn Asn Leu Asp Ser Lys Val Gly
115 120 125

Gly Asn Tyr Asn Tyr Leu Tyr Arg Leu Phe Arg Lys Ser Asn Leu Lys
130 135 140

Pro Phe Glu Arg Asp Ile Ser Thr Glu Ile Tyr Gln Ala Gly Ser Thr
145 150 155 160

Pro Cys Asn Gly Val Lys Gly Phe Asn Cys Tyr Phe Pro Leu Gln Ser
165 170 175

Tyr Gly Phe Gln Pro Thr Tyr Gly Val Gly Tyr Gln Pro Tyr Arg Val
180 185 190

Val Val Leu Ser Phe Glu Leu Leu His Ala Pro Ala Thr Val Cys Gly
195 200 205

Pro Lys Lys Ser Thr Asn Leu Val Lys Asn Lys
210 215

<210> SEQ ID NO 3
<211> LENGTH: 219
<212> TYPE: PRT
<213> ORGANISM: SARS-CoV-2

<400> SEQUENCE: 3

Arg Val Gln Pro Thr Glu Ser Ile Val Arg Phe Pro Asn Ile Thr Asn
1 5 10 15

Leu Cys Pro Phe Gly Glu Val Phe Asn Ala Thr Arg Phe Ala Ser Val
20 25 30

Tyr Ala Trp Asn Arg Lys Arg Ile Ser Asn Cys Val Ala Asp Tyr Ser
35 40 45

Val Leu Tyr Asn Ser Ala Ser Phe Ser Thr Phe Lys Cys Tyr Gly Val
50 55 60

Ser Pro Thr Lys Leu Asn Asp Leu Cys Phe Thr Asn Val Tyr Ala Asp
65 70 75 80

Ser Phe Val Ile Arg Gly Asp Glu Val Arg Gln Ile Ala Pro Gly Gln
85 90 95

Thr Gly Lys Ile Ala Asp Tyr Asn Tyr Lys Leu Pro Asp Asp Phe Thr
100 105 110

Gly Cys Val Ile Ala Trp Asn Ser Asn Asn Leu Asp Ser Lys Val Gly
115 120 125

```
Gly Asn Tyr Asn Tyr Arg Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Gln Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys
    210                 215


<210> SEQ ID NO 4
<211> LENGTH: 658
<212> TYPE: PRT
<213> ORGANISM: Artificial Sequence
<220> FEATURE:
<223> OTHER INFORMATION: SARS-CoV-2

<400> SEQUENCE: 4

Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270
```

-continued

```
Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Asn Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Lys Gly Phe Asn Cys Tyr Phe Pro Leu Gln Ser Tyr Gly Phe Gln
385                 390                 395                 400

Pro Thr Tyr Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys Arg Val Gln Pro Thr Glu Ser Ile Val
        435                 440                 445

Arg Phe Pro Asn Ile Thr Asn Leu Cys Pro Phe Gly Glu Val Phe Asn
    450                 455                 460

Ala Thr Arg Phe Ala Ser Val Tyr Ala Trp Asn Arg Lys Arg Ile Ser
465                 470                 475                 480

Asn Cys Val Ala Asp Tyr Ser Val Leu Tyr Asn Ser Ala Ser Phe Ser
                485                 490                 495

Thr Phe Lys Cys Tyr Gly Val Ser Pro Thr Lys Leu Asn Asp Leu Cys
            500                 505                 510

Phe Thr Asn Val Tyr Ala Asp Ser Phe Val Ile Arg Gly Asp Glu Val
        515                 520                 525

Arg Gln Ile Ala Pro Gly Gln Thr Gly Lys Ile Ala Asp Tyr Asn Tyr
    530                 535                 540

Lys Leu Pro Asp Asp Phe Thr Gly Cys Val Ile Ala Trp Asn Ser Asn
545                 550                 555                 560

Asn Leu Asp Ser Lys Val Gly Gly Asn Tyr Asn Tyr Arg Tyr Arg Leu
                565                 570                 575

Phe Arg Lys Ser Asn Leu Lys Pro Phe Glu Arg Asp Ile Ser Thr Glu
            580                 585                 590

Ile Tyr Gln Ala Gly Ser Thr Pro Cys Asn Gly Val Gln Gly Phe Asn
        595                 600                 605

Cys Tyr Phe Pro Leu Gln Ser Tyr Gly Phe Gln Pro Thr Asn Gly Val
    610                 615                 620

Gly Tyr Gln Pro Tyr Arg Val Val Val Leu Ser Phe Glu Leu Leu His
625                 630                 635                 640

Ala Pro Ala Thr Val Cys Gly Pro Lys Lys Ser Thr Asn Leu Val Lys
                645                 650                 655

Asn Lys
```

<210> SEQ ID NO 5
<211> LENGTH: 658
<212> TYPE: PRT
<213> ORGANISM: Artificial Sequence -continued
<220> FEATURE:
<223> OTHER INFORMATION: SARS-CoV-2

<400> SEQUENCE: 5

```
Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Asn Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Lys Gly Phe Asn Cys Tyr Phe Pro Leu Gln Ser Tyr Gly Phe Gln
385                 390                 395                 400
```

Pro Thr Tyr Gly Val Gly Tyr Gln Pro Tyr Arg Val Val Val Leu Ser
405 410 415

Phe Glu Leu Leu His Ala Pro Ala Thr Val Cys Gly Pro Lys Lys Ser
420 425 430

Thr Asn Leu Val Lys Asn Lys Arg Val Gln Pro Thr Glu Ser Ile Val
435 440 445

Arg Phe Pro Asn Ile Thr Asn Leu Cys Pro Phe Gly Glu Val Phe Asn
450 455 460

Ala Thr Arg Phe Ala Ser Val Tyr Ala Trp Asn Arg Lys Arg Ile Ser
465 470 475 480

Asn Cys Val Ala Asp Tyr Ser Val Leu Tyr Asn Ser Ala Ser Phe Ser
485 490 495

Thr Phe Lys Cys Tyr Gly Val Ser Pro Thr Lys Leu Asn Asp Leu Cys
500 505 510

Phe Thr Asn Val Tyr Ala Asp Ser Phe Val Ile Arg Gly Asp Glu Val
515 520 525

Arg Gln Ile Ala Pro Gly Gln Thr Gly Lys Ile Ala Asp Tyr Asn Tyr
530 535 540

Lys Leu Pro Asp Asp Phe Thr Gly Cys Val Ile Ala Trp Asn Ser Asn
545 550 555 560

Asn Leu Asp Ser Lys Val Gly Gly Asn Tyr Asn Tyr Leu Tyr Arg Leu
565 570 575

Phe Arg Lys Ser Asn Leu Lys Pro Phe Glu Arg Asp Ile Ser Thr Glu
580 585 590

Ile Tyr Gln Ala Gly Ser Thr Pro Cys Asn Gly Val Glu Gly Phe Asn
595 600 605

Cys Tyr Phe Pro Leu Gln Ser Tyr Gly Phe Gln Pro Thr Asn Gly Val
610 615 620

Gly Tyr Gln Pro Tyr Arg Val Val Val Leu Ser Phe Glu Leu Leu His
625 630 635 640

Ala Pro Ala Thr Val Cys Gly Pro Lys Lys Ser Thr Asn Leu Val Lys
645 650 655

Asn Lys

<210> SEQ ID NO 6
<211> LENGTH: 658
<212> TYPE: PRT
<213> ORGANISM: Artificial Sequence
<220> FEATURE:
<223> OTHER INFORMATION: SARS-CoV-2

<400> SEQUENCE: 6

Met Arg Val Gln Pro Thr Glu Ser Ile Val Arg Phe Pro Asn Ile Thr
1 5 10 15

Asn Leu Cys Pro Phe Gly Glu Val Phe Asn Ala Thr Arg Phe Ala Ser
20 25 30

Val Tyr Ala Trp Asn Arg Lys Arg Ile Ser Asn Cys Val Ala Asp Tyr
35 40 45

Ser Val Leu Tyr Asn Ser Ala Ser Phe Ser Thr Phe Lys Cys Tyr Gly
50 55 60

Val Ser Pro Thr Lys Leu Asn Asp Leu Cys Phe Thr Asn Val Tyr Ala
65 70 75 80

Asp Ser Phe Val Ile Arg Gly Asp Glu Val Arg Gln Ile Ala Pro Gly
85 90 95

-continued

```
Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Asn Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Lys Gly Phe Asn Cys Tyr Phe Pro Leu Gln Ser Tyr Gly Phe Gln
385                 390                 395                 400

Pro Thr Tyr Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys Arg Val Gln Pro Thr Glu Ser Ile Val
        435                 440                 445

Arg Phe Pro Asn Ile Thr Asn Leu Cys Pro Phe Gly Glu Val Phe Asn
    450                 455                 460

Ala Thr Arg Phe Ala Ser Val Tyr Ala Trp Asn Arg Lys Arg Ile Ser
465                 470                 475                 480

Asn Cys Val Ala Asp Tyr Ser Val Leu Tyr Asn Ser Ala Ser Phe Ser
                485                 490                 495

Thr Phe Lys Cys Tyr Gly Val Ser Pro Thr Lys Leu Asn Asp Leu Cys
            500                 505                 510

Phe Thr Asn Val Tyr Ala Asp Ser Phe Val Ile Arg Gly Asp Glu Val
```

```
        515                 520                 525

Arg Gln Ile Ala Pro Gly Gln Thr Gly Asn Ile Ala Asp Tyr Asn Tyr
    530                 535                 540

Lys Leu Pro Asp Asp Phe Thr Gly Cys Val Ile Ala Trp Asn Ser Asn
545                 550                 555                 560

Asn Leu Asp Ser Lys Val Gly Gly Asn Tyr Asn Tyr Leu Tyr Arg Leu
                565                 570                 575

Phe Arg Lys Ser Asn Leu Lys Pro Phe Glu Arg Asp Ile Ser Thr Glu
            580                 585                 590

Ile Tyr Gln Ala Gly Ser Thr Pro Cys Asn Gly Val Lys Gly Phe Asn
        595                 600                 605

Cys Tyr Phe Pro Leu Gln Ser Tyr Gly Phe Gln Pro Thr Tyr Gly Val
    610                 615                 620

Gly Tyr Gln Pro Tyr Arg Val Val Val Leu Ser Phe Glu Leu Leu His
625                 630                 635                 640

Ala Pro Ala Thr Val Cys Gly Pro Lys Lys Ser Thr Asn Leu Val Lys
                645                 650                 655

Asn Lys


<210> SEQ ID NO 7
<211> LENGTH: 658
<212> TYPE: PRT
<213> ORGANISM: Artificial Sequence
<220> FEATURE:
<223> OTHER INFORMATION: SARS-CoV-2

<400> SEQUENCE: 7

Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Asn Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Lys Gly Phe Asn Cys Tyr Phe Pro Leu Gln
                165                 170                 175

Ser Tyr Gly Phe Gln Pro Thr Tyr Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220
```

-continued

```
Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Lys Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Glu Gly Phe Asn Cys Tyr Phe Pro Leu Gln Ser Tyr Gly Phe Gln
385                 390                 395                 400

Pro Thr Asn Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys Arg Val Gln Pro Thr Glu Ser Ile Val
        435                 440                 445

Arg Phe Pro Asn Ile Thr Asn Leu Cys Pro Phe Gly Glu Val Phe Asn
    450                 455                 460

Ala Thr Arg Phe Ala Ser Val Tyr Ala Trp Asn Arg Lys Arg Ile Ser
465                 470                 475                 480

Asn Cys Val Ala Asp Tyr Ser Val Leu Tyr Asn Ser Ala Ser Phe Ser
                485                 490                 495

Thr Phe Lys Cys Tyr Gly Val Ser Pro Thr Lys Leu Asn Asp Leu Cys
            500                 505                 510

Phe Thr Asn Val Tyr Ala Asp Ser Phe Val Ile Arg Gly Asp Glu Val
        515                 520                 525

Arg Gln Ile Ala Pro Gly Gln Thr Gly Asn Ile Ala Asp Tyr Asn Tyr
    530                 535                 540

Lys Leu Pro Asp Asp Phe Thr Gly Cys Val Ile Ala Trp Asn Ser Asn
545                 550                 555                 560

Asn Leu Asp Ser Lys Val Gly Gly Asn Tyr Asn Tyr Leu Tyr Arg Leu
                565                 570                 575

Phe Arg Lys Ser Asn Leu Lys Pro Phe Glu Arg Asp Ile Ser Thr Glu
            580                 585                 590

Ile Tyr Gln Ala Gly Ser Thr Pro Cys Asn Gly Val Lys Gly Phe Asn
        595                 600                 605

Cys Tyr Phe Pro Leu Gln Ser Tyr Gly Phe Gln Pro Thr Tyr Gly Val
    610                 615                 620

Gly Tyr Gln Pro Tyr Arg Val Val Val Leu Ser Phe Glu Leu Leu His
625                 630                 635                 640
```

```
Ala Pro Ala Thr Val Cys Gly Pro Lys Lys Ser Thr Asn Leu Val Lys
                645                 650                 655

Asn Lys


<210> SEQ ID NO 8
<211> LENGTH: 658
<212> TYPE: PRT
<213> ORGANISM: Artificial Sequence
<220> FEATURE:
<223> OTHER INFORMATION: SARS-CoV-2

<400> SEQUENCE: 8

Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Asn Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Lys Gly Phe Asn Cys Tyr Phe Pro Leu Gln
                165                 170                 175

Ser Tyr Gly Phe Gln Pro Thr Tyr Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Asn Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
```

-continued

```
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Lys Gly Phe Asn Cys Tyr Phe Pro Leu Gln Ser Tyr Gly Phe Gln
385                 390                 395                 400

Pro Thr Tyr Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys Arg Val Gln Pro Thr Glu Ser Ile Val
        435                 440                 445

Arg Phe Pro Asn Ile Thr Asn Leu Cys Pro Phe Gly Glu Val Phe Asn
    450                 455                 460

Ala Thr Arg Phe Ala Ser Val Tyr Ala Trp Asn Arg Lys Arg Ile Ser
465                 470                 475                 480

Asn Cys Val Ala Asp Tyr Ser Val Leu Tyr Asn Ser Ala Ser Phe Ser
                485                 490                 495

Thr Phe Lys Cys Tyr Gly Val Ser Pro Thr Lys Leu Asn Asp Leu Cys
            500                 505                 510

Phe Thr Asn Val Tyr Ala Asp Ser Phe Val Ile Arg Gly Asp Glu Val
        515                 520                 525

Arg Gln Ile Ala Pro Gly Gln Thr Gly Asn Ile Ala Asp Tyr Asn Tyr
    530                 535                 540

Lys Leu Pro Asp Asp Phe Thr Gly Cys Val Ile Ala Trp Asn Ser Asn
545                 550                 555                 560

Asn Leu Asp Ser Lys Val Gly Gly Asn Tyr Asn Tyr Leu Tyr Arg Leu
                565                 570                 575

Phe Arg Lys Ser Asn Leu Lys Pro Phe Glu Arg Asp Ile Ser Thr Glu
            580                 585                 590

Ile Tyr Gln Ala Gly Ser Thr Pro Cys Asn Gly Val Lys Gly Phe Asn
        595                 600                 605

Cys Tyr Phe Pro Leu Gln Ser Tyr Gly Phe Gln Pro Thr Tyr Gly Val
    610                 615                 620

Gly Tyr Gln Pro Tyr Arg Val Val Val Leu Ser Phe Glu Leu Leu His
625                 630                 635                 640

Ala Pro Ala Thr Val Cys Gly Pro Lys Lys Ser Thr Asn Leu Val Lys
                645                 650                 655

Asn Lys


<210> SEQ ID NO 9
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 9

atgagagtgc agcctaccga gagcattgtc agattcccta acatcaccaa tctgtgccct      60

ttcggcgagg tgttcaacgc tacaagattt gctagcgtgt acgcttggaa cagaaagaga     120

atcagcaatt gcgtcgccga ctacagcgtg ctgtacaaca gcgcctcctt cagcaccttc     180

aagtgctacg gcgtcagccc tacaaaactg aatgacctgt gctttacaaa tgtgtatgcc     240
```

-continued

```
gatagcttcg tcatcagagg cgacgaggtg aggcaaatcg ctcctggcca aaccggcaag    300

atcgccgact acaattacaa gctgcctgac gatttcaccg gatgcgtgat tgcctggaac    360

agcaacaacc tggacagcaa ggtgggcggc aactacaact acctgtacag actgtttaga    420

aaaagcaacc tgaagccttt cgagagagac atcagcaccg agatctacca agccggcagc    480

acaccttgca acggcgtgga gggattcaac tgctatttcc ctctgcagag ctacggcttt    540

cagcctacca acggcgtggg ctatcagcct tatagagtcg tggtgctcag cttcgaactc    600

ctgcacgccc ctgctacagt gtgtggccct aagaagtcca ccaacctggt gaagaataag    660

agagtgcaac ctaccgagag catcgtgaga ttccccaata ttaccaacct gtgccccttt    720

ggcgaagtgt tcaacgccac aagattcgct agcgtgtacg cctggaacag aaagagaatc    780

agcaactgcg tggccgacta cagcgtgctc tacaactccg ctagcttcag cacctttaag    840

tgctacggcg tgagccctac caagctgaac gacctgtgct ttaccaacgt ctatgctgac    900

agctttgtga tcagaggcga cgaggtgaga cagatcgctc ccggacagac cggcaatatc    960

gccgattaca actacaagct gcccgacgat ttcaccggat gcgtgatcgc ctggaacagc   1020

aacaatctgg actccaaggt gggaggcaat tacaattacc tgtacagact gtttagaaaa   1080

tccaacctga agcctttcga gagagacatt tccaccgaga tctaccaagc cggctccaca   1140

ccttgcaatg gagtgaaggg cttcaactgc tacttccctc tgcagagcta cggctttcag   1200

cctacatacg gagtcggcta tcagccttac agagtcgtcg tcctgagctt cgagctcctg   1260

cacgcccccg ccaccgtctg cggacctaag aagtccacaa acctcgtcaa aaacaagaga   1320

gtgcagccta ccgagagcat cgtgaggttt cctaacatca ccaacctgtg ccctttcggc   1380

gaggtcttta acgccacaag attcgctagc gtctacgcct ggaacagaaa gaggattagc   1440

aattgtgtcg ccgactacag cgtgctgtac aacagcgcta gcttcagcac cttcaagtgc   1500

tacggcgtga gccctaccaa gctgaacgac ctgtgcttta caaacgtgta tgccgacagc   1560

ttcgtgatta ggggcgacga ggtgaggcaa atcgctcctg gccaaaccgg caagatcgcc   1620

gactacaact acaagctgcc tgacgatttc accggctgcg tgatcgcctg gaacagcaac   1680

aacctggata gcaaggtggg cggcaattac aactacagat atagactgtt cagaaagagc   1740

aacctgaagc ctttcgagag agacatctcc accgagatct atcaagccgg cagcacacct   1800

tgcaacggag tgcaaggctt caactgctat ttccctctgc aatcctacgg ctttcagcct   1860

accaacggag tgggctatca gccttacaga gtcgtcgtgc tgagcttcga gctgctgcac   1920

gcccctgcca cagtgtgcgg acctaaaaag agcacaaatc tggtgaagaa caagtga      1977
```

<210> SEQ ID NO 10
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 10

```
atgagagtgc agcctacaga gagcattgtg agattcccta acatcacaaa cctgtgccct     60

ttcggcgagg tgttcaacgc cacaagattc gctagcgtgt acgcctggaa cagaaaaaga    120

attagcaatt gcgtcgccga ttacagcgtg ctgtataaca gcgcttcctt cagcaccttc    180

aagtgctacg gcgtcagccc tacaaagctg aacgacctgt gcttcacaaa cgtgtatgcc    240

gacagcttcg tgatcagagg cgacgaggtg aggcaaatcg ctcctggcca aaccggcaag    300

atcgccgact acaattacaa gctgcctgat gacttcaccg gatgcgtgat tgcctggaac    360
```

```
agcaacaacc tggacagcaa agtcggagga aactacaact acctgtacag actgttcaga    420
aagagcaacc tgaagccttt cgagagagac atcagcaccg agatctacca agccggctcc    480
acaccttgca acggcgtgga gggattcaac tgctacttcc ctctgcagag ctacggcttt    540
cagcccacca acggcgtggg ctatcagcct tacagagtgg tcgtcctgag ctttgagctg    600
ctccacgccc ctgccaccgt ctgcggcccc aaaaaaagca ccaatctggt gaagaacaag    660
agggtgcagc ctacagagag catcgtgaga ttccctaaca ttaccaacct gtgccctttc    720
ggagaagtgt ttaacgccac aagattcgcc tccgtctacg cttggaatag aaagaggatc    780
agcaactgcg tggccgacta cagcgtgctg tacaattccg cctccttcag caccttcaag    840
tgttacggcg tgagccctac caagctgaac gacctgtgct tcaccaacgt gtacgccgat    900
agcttcgtga ttagaggcga cgaggtgagg cagatcgccc ctggacaaac cggcaacatt    960
gctgactaca attacaagct gcctgacgac ttcaccggct gcgtgatcgc ctggaacagc   1020
aacaacctgg acagcaaggt cggaggcaat tacaattacc tctatagact gttcagaaaa   1080
agcaatctca agcctttcga aagagacatt agcaccgaga tctaccaagc cggcagcacc   1140
ccctgcaacg gcgtgaaagg attcaactgc tacttccccc tgcagagcta cggctttcag   1200
cccacctacg gagtgggcta tcaaccctac agagtggtcg tgctctcctt cgagctgctg   1260
catgcccctg ccacagtgtg cggacctaaa aagtccacca acctcgtgaa gaacaagaga   1320
gtgcagccta cagagagcat cgtgaggttc cccaacatca ccaacctgtg ccctttcggc   1380
gaggtgttta acgctacaag attcgctagc gtgtacgctt ggaacagaaa gagaatctcc   1440
aattgcgtgg ccgactacag cgtgctgtac aacagcgcta gcttcagcac cttcaagtgc   1500
tacggagtgt cccctaccaa gctgaacgac ctgtgcttca ccaacgtgta cgccgatagc   1560
ttcgtgatta gaggagacga agtgagacag attgctcctg gacagaccgg caagatcgcc   1620
gactacaatt acaagctgcc tgatgacttt accggctgtg tgattgcctg gaacagcaac   1680
aacctggaca gcaaggtggg cggcaactac aactatctgt acagactctt cagaaagagc   1740
aatctgaagc cttttgaaag ggacatcagc accgagatct atcaagccgg cagcacccct   1800
tgcaacggag tcgagggctt caactgctac tttcctctgc agagctatgg ctttcagcct   1860
accaacggcg tcggatatca gccttacaga gtcgtggtgc tgagcttcga gctgctccac   1920
gcccctgcca ccgtctgcgg ccctaagaaa agcaccaacc tggtcaagaa caaatga      1977
```

<210> SEQ ID NO 11
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 11

```
atgagagtgc agcctacaga gagcattgtg agattcccta acatcaccaa tctgtgccct     60
ttcggcgagg tgttcaacgc cacaagattc gctagcgtgt acgcctggaa cagaaagagg    120
atctccaatt gcgtggctga ctatagcgtg ctgtacaata gcgctagctt cagcaccttc    180
aagtgctacg gcgtcagccc tacaaagctg aacgacctgt gcttcacaaa cgtgtatgcc    240
gacagcttcg tgatcagagg cgacgaggtg aggcaaatcg ctcctggcca aaccggcaag    300
atcgccgact ataattataa gctgcctgat gacttcaccg gctgcgtcat cgcctggaac    360
agcaataatc tggacagcaa ggtcggaggc aactacaact acctgtacag actgttcaga    420
```

-continued

```
aagagcaacc tgaagccttt cgagagagac atcagcaccg agatttacca agccggctcc    480

accccttgca acggcgtgga aggcttcaac tgctacttcc ctctgcagtc ctacggcttt    540

cagcctacaa acggcgtggg ctaccaaccc tacagagtcg tggtgctcag cttcgagctg    600

ctgcatgccc ctgctaccgt gtgcggcccc aaaaagagca ccaacctcgt gaagaataag    660

agagtgcagc ctaccgagag catcgtcaga ttccctaaca tcaccaatct ctgccccttc    720

ggcgaggtgt tcaacgccac aagattcgct agcgtctacg cttggaatag aaagagaatc    780

agcaactgtg tggccgacta tagcgtgctg tacaacagcg ctagctttag cacctttaag    840

tgctacggcg tgtcccctac caagctgaac gacctgtgct tcacaaatgt gtacgccgac    900

agcttcgtga tcagaggaga cgaggtgagg cagatcgccc ctggacaaac cggcaatatt    960

gccgactaca actacaagct gcccgacgac ttcaccggct gcgtgatcgc ctggaacagc   1020

aacaacctcg acagcaaagt gggaggcaat tacaactacc tgtatagact gtttagaaag   1080

agcaacctga agcctttcga gagggacatc tccaccgaga tctaccaagc cggcagcacc   1140

ccttgtaacg gcgtgaaggg cttcaactgt tacttccctc tgcagagcta tggctttcag   1200

cctacatacg gagtgggcta tcagccttac agagtggtgg tcctctcctt tgaactcctg   1260

catgcccctg ccacagtgtg cggacctaaa aagagcacca acctcgtgaa gaataagaga   1320

gtgcagccta ccgagagcat cgtgagattc cccaatatca ccaacctgtg tcctttcggc   1380

gaggtgttca atgccacaag attcgctagc gtctatgcct ggaacagaaa gagaatctcc   1440

aattgcgtgg ccgactacag cgtgctgtac aacagcgcta gcttcagcac cttcaagtgc   1500

tacggagtga gccctaccaa gctgaacgac ctctgcttta ccaatgtgta cgccgatagc   1560

ttcgtcatta gaggagacga ggtgagacag attgctcctg gacagaccgg caacatcgcc   1620

gactacaact acaagctgcc tgacgatttt accggctgtg tgatcgcctg gaacagcaac   1680

aacctggaca gcaaggtcgg cggcaactac aactatctgt acagactgtt tagaaagagc   1740

aacctgaagc ctttcgaaag ggacatcagc accgagatct atcaagccgg ctccacccct   1800

tgcaacggcg tcaagggctt taactgctac ttccctctgc agagctacgg ctttcagcct   1860

acctacggcg tcggatatca gccttataga gtggtcgtgc tgagcttcga gctgctccac   1920

gcccctgcca ccgtctgcgg ccctaaaaag agcaccaacc tggtcaagaa caaatga      1977
```

```
<210> SEQ ID NO 12
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 12
```

```
atgagagtgc agcccacaga gagcattgtg agattcccca acatcaccaa tctgtgcccc     60

ttcggcgagg tgttcaacgc cacaagattc gctagcgtgt acgcctggaa cagaaagcgg    120

atctccaatt gcgtggctga ctatagcgtg ctgtacaata gcgctagctt cagcaccttc    180

aagtgctacg gcgtcagccc cacaaagctg aacgacctgt gcttcacaaa cgtgtatgcc    240

gacagcttcg tgatcagagg cgacgaggtg cggcaaatcg ctcccggcca aaccggcaag    300

atcgccgact ataattataa gctgcccgat gacttcaccg gctgcgtcat cgcctggaac    360

agcaataatc tggacagcaa ggtcgggggc aactacaact acctgtacag actgttcaga    420

aagagcaacc tgaagccctt cgagagagac atcagcaccg agatttacca agccggctcc    480

accccctgca acggcgtgga aggcttcaac tgctacttcc ccctgcagtc ctacggcttt    540
```

```
cagcccacaa acggcgtggg ctaccaacct tacagagtcg tggtgctcag cttcgagctg    600

ctgcatgccc ccgctaccgt gtgcggccct aaaaagagca ccaacctcgt gaagaataag    660

agagtgcagc ccaccgagag catcgtcaga ttccccaaca tcaccaatct ctgccctttc    720

ggcgaggtgt tcaacgccac aagattcgct agcgtctacg cttggaaccg gaagagaatc    780

agcaactgtg tggccgacta tagcgtgctg tacaacagcg ctagctttag cacctttaag    840

tgctacggcg tgtcccccac caagctgaac gacctgtgct tcacaaatgt gtacgccgac    900

agcttcgtga tcagagggga cgaggtgcgg cagatcgccc ccgggcaaac cggcaatatt    960

gccgactaca actacaagct gcctgacgac ttcaccggct gcgtgatcgc ctggaacagc   1020

aacaacctcg acagcaaagt ggggggcaat tacaactacc tgtatagact gtttagaaag   1080

agcaacctga agcccttcga gcgggacatc tccaccgaga tctaccaagc cggcagcacc   1140

ccctgtaacg gcgtgaaggg cttcaactgt tacttccccc tgcagagcta tggctttcag   1200

cccacatacg gggtgggcta tcagccctac agagtggtgg tcctctcctt tgaactcctg   1260

catgcccccg ccacagtgtg cgggcccaaa aagagcacca acctcgtgaa gaataagaga   1320

gtgcagccca ccgagagcat cgtgagattc cctaatatca ccaacctgtg tcccttcggc   1380

gaggtgttca atgccacaag attcgctagc gtctatgcct ggaacagaaa gagaatctcc   1440

aattgcgtgg ccgactacag cgtgctgtac aacagcgcta gcttcagcac cttcaagtgc   1500

tacggggtga gccccaccaa gctgaacgac ctctgcttta ccaatgtgta cgccgatagc   1560

ttcgtcatcc ggggggacga ggtgagacag attgctcccg ggcagaccgg caacatcgcc   1620

gactacaact acaagctgcc cgacgatttt accggctgtg tgatcgcctg gaacagcaac   1680

aacctggaca gcaaggtcgg cggcaactac aactatctgt acagactgtt tagaaagagc   1740

aacctgaagc ccttcgaacg ggacatcagc accgagatct atcaagccgg ctccaccccc   1800

tgcaacggcg tcaagggctt taactgctac ttcccccctgc agagctacgg ctttcagccc   1860

acctacggcg tcgggtatca gccctaccgg gtggtcgtgc tgagcttcga gctgctccac   1920

gcccccgcca ccgtctgcgg ccccaaaaag agcaccaacc tggtcaagaa caaatga      1977
```

<210> SEQ ID NO 13
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 13

```
atgagagtgc agcctaccga gagcatcgtg agatttccta atatcaccaa tctctgcccc     60

ttcggcgagg tgtttaacgc cacaagattt gctagcgtgt acgcctggaa cagaaaaaga    120

atctccaact gcgtggccga ctacagcgtc ctgtacaata gcgctagctt cagcaccttc    180

aagtgctacg gcgtctcccc tacaaagctg aatgacctgt gttttaccaa cgtgtatgcc    240

gacagcttcg tgattagagg cgatgaggtg aggcagatcg cccctggaca gaccggcaag    300

atcgctgatt acaactacaa gctgcctgac gacttcaccg gctgcgtgat cgcctggaac    360

agcaacaacc tggatagcaa ggtgggcggc aactacaact atctgtacag actgttcaga    420

aaaagcaacc tgaagccttt tgagagagac atcagcacag agatctacca agccggcagc    480

acccccttgca acggcgtgga aggatttaac tgctatttcc ctctgcagag ctatggcttc    540

caacctacca acggagtggg ctatcagccc tacagagtgg tcgtgctgag cttcgagctg    600
```

```
ctgcacgctc ctgccaccgt gtgcggcccc aaaaagtcca ccaacctggt gaagaataaa    660
agagtgcagc ctaccgaatc catcgtgaga ttccctaaca tcaccaacct gtgccctttc    720
ggcgaggtct tcaacgccac aagatttgct agcgtgtacg cctggaacag aaagagaatc    780
agcaactgcg tggccgacta cagcgtcctg tacaacagcg cctccttcag caccttcaaa    840
tgctacggcg tgtcccctac caagctgaat gacctgtgct ttaccaacgt gtacgccgac    900
agctttgtga tcagaggcga cgaggtgaga cagattgctc ctggacagac cggcaacatt    960
gccgattaca attacaagct gcctgatgat ttcaccggct gtgtgatcgc ctggaacagc   1020
aacaacctgg acagcaaggt gggcggcaac tataattacc tgtatagact gttcagaaaa   1080
agcaacctga agcctttcga gagagacatc tccaccgaaa tttaccaagc cggatccaca   1140
ccttgcaacg gcgtgaaggg cttcaattgt tacttccctc tgcaaagcta cggctttcag   1200
cctacatacg gagtgggcta ccaaccctac agagtggtcg tgctgagctt cgagctgctc   1260
cacgcccctg ccaccgtgtg cggccctaaa aagagcacca acctggtgaa gaataagaga   1320
gtgcaaccca cagagagcat tgtgagattc cctaacatca caaatctgtg ccctttcggc   1380
gaggtgttca acgccacaag attcgctagc gtgtacgctt ggaacagaaa gagaatcagc   1440
aactgtgtgg ctgactacag cgtgctctac aacagcgctt ccttcagcac ctttaaatgc   1500
tacggcgtga gccccacaaa gctcaacgac ctgtgcttca ccaacgtcta cgccgacagc   1560
ttcgtgatta gaggagacga agtgagacag atcgctcctg gacagaccgg caatatcgcc   1620
gactacaact acaaactgcc tgacgacttc accggctgcg tgatcgcctg gaacagcaat   1680
aatctcgaca gcaaggtcgg cggcaactac aattacctgt atagactgtt tagaaagagc   1740
aacctgaagc ccttcgagag agacatctcc accgagatct accaagccgg ctccacacct   1800
tgcaacggcg tgaagggctt caactgctac ttccctctgc agagctacgg cttccaacct   1860
acctacggag tgggctatca gccttataga gtggtcgtgc tgagcttcga actgctgcac   1920
gcccccgcca ccgtgtgcgg ccccaaaaag agcacaaacc tggtgaagaa caagtga      1977
```

<210> SEQ ID NO 14
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 14

```
atgagagtgc agcctaccga gagcatcgtg agattcccta acatcacaaa cctctgccct     60
tttggagagg tcttcaacgc cacaagattc gcctccgtgt atgcctggaa cagaaagaga    120
atcagcaatt gcgtggctga ctacagcgtg ctgtacaact ccgctagctt tagcaccttc    180
aagtgctacg gcgtgagccc taccaaactc aacgatctgt gctttaccaa cgtctatgcc    240
gacagctttg tgatcagagg cgacgaggtc agacaaatcg cccccggaca gaccggcaag    300
atcgccgact acaactataa actgcctgac gacttcaccg gctgcgtgat cgcctggaac    360
agcaacaacc tggactccaa ggtgggcggc aactacaact acctgtacag actcttcaga    420
aagagcaacc tgaaaccttt cgaaagagac atcagcaccg aaatctacca agccggcagc    480
acccccttgca acggcgtgga gggctttaat tgctactttc ctctgcaaag ctacggcttt   540
cagcccacca acggagtggg ctatcagcct tatagagtcg tcgtgctgag ctttgagctg    600
ctgcacgccc ctgccaccgt ctgcggccct aaaaagagca caaatctggt caagaacaag    660
agagtgcagc ctaccgagag cattgtgaga tttcctaaca tcaccaatct gtgccctttc    720
```

```
ggcgaggtgt tcaatgccac aagatttgct agcgtctacg cctggaacag aaaaagaatc    780

agcaactgcg tggccgacta cagcgtgctg tacaactccg ctagcttcag cacctttaag    840

tgctacggcg tcagccctac caaactgaac gacctctgct ttaccaacgt gtatgccgac    900

agcttcgtga tcagaggaga cgaggtgaga cagatcgccc ctggacagac cggcaacatc    960

gccgattaca attacaaact gcccgacgac ttcaccggct gtgtgattgc ttggaactcc   1020

aacaacctcg acagcaaggt gggcggcaac tacaactacc tgtatagact gttcagaaag   1080

agcaacctga agcctttcga gagagatatc agcaccgaga tctaccaagc cggcagcaca   1140

ccttgtaacg gcgtgaaagg cttcaattgt tatttccccc tgcagagcta cggctttcag   1200

cctacctatg gcgtgggata ccaaccttac agagtggtcg tgctgagctt cgaactgctg   1260

cacgcccctg ccaccgtgtg cggcccccaaa aagagcacca atctggtgaa gaacaaaaga   1320

gtgcaaccta ccgagagcat cgtgagattc cccaatatta caaacctgtg cccctttggc   1380

gaggtgttca acgccacaag attcgctagc gtgtacgcct ggaacagaaa gagaatcagc   1440

aactgcgtgg ctgactacag cgtgctgtac aacagcgcct ccttcagcac attcaagtgc   1500

tacggagtca gccctaccaa gctgaatgat ctgtgtttca caaacgtgta cgccgacagc   1560

ttcgtgatca gaggcgacga agtgagacag attgcccctg gacagaccgg caacatcgcc   1620

gactacaatt acaagctgcc tgacgatttc accggctgcg tcatcgcctg gaacagcaac   1680

aacctggact ccaaagtggg cggcaactac aattacctgt atagactgtt cagaaagtcc   1740

aatctcaagc ccttcgagag agacatcagc accgagattt atcaagccgg cagcacccct   1800

tgcaatggag tgaaaggctt caactgctac ttccctctgc agagctacgg atttcagcct   1860

acctacggag tgggctatca gccttacaga gtggtcgtgc tgagctttga gctgctgcac   1920

gctcctgcca ccgtgtgcgg ccctaaaaag agcaccaacc tggtgaagaa caagtga      1977
```

<210> SEQ ID NO 15
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 15

```
atgagagtgc agcctacaga gagcattgtg agattcccta acatcacaaa cctgtgccct     60

ttcggcgagg tgttcaacgc cacaagattc gctagcgtgt acgcctggaa cagaaaaaga    120

attagcaatt gcgtcgccga ttacagcgtg ctgtataaca gcgcttcctt cagcaccttc    180

aagtgctacg gcgtcagccc tacaaagctg aacgacctgt gcttcacaaa cgtgtatgcc    240

gacagcttcg tgatcagagg cgacgaggtg aggcaaatcg ctcctggcca aaccggcaac    300

atcgccgact acaattacaa gctgcctgat gacttcaccg gatgcgtgat tgcctggaac    360

agcaacaacc tggacagcaa agtcggagga aactacaact acctgtacag actgttcaga    420

aagagcaacc tgaagccttt cgagagagac atcagcaccg agatctacca agccggctcc    480

acaccttgca acggcgtgaa gggattcaac tgctacttcc ctctgcagag ctacggcttt    540

cagcccacct acggcgtggg ctatcagcct tacagagtgg tcgtcctgag ctttgagctg    600

ctccacgccc ctgccaccgt ctgcggcccc aaaaaaagca ccaatctggt gaagaacaag    660

agggtgcagc ctacagagag catcgtgaga ttccctaaca ttaccaacct gtgccctttc    720

ggagaagtgt ttaacgccac aagattcgcc tccgtctacg cttggaatag aaagaggatc    780
```

agcaactgcg tggccgacta cagcgtgctg tacaattccg cctccttcag caccttcaag 840
tgttacggcg tgagccctac caagctgaac gacctgtgct tcaccaacgt gtacgccgat 900
agcttcgtga ttagaggcga cgaggtgagg cagatcgccc ctggacaaac cggcaagatt 960
gctgactaca attacaagct gcctgacgac ttcaccggct gcgtgatcgc ctggaacagc 1020
aacaacctgg acagcaaggt cggaggcaat tacaattacc tctatagact gttcagaaaa 1080
agcaatctca agcctttcga aagagacatt agcaccgaga tctaccaagc cggcagcacc 1140
ccctgcaacg gcgtggaagg attcaactgc tacttccccc tgcagagcta cggctttcag 1200
cccaccaacg gagtgggcta tcaaccctac agagtggtcg tgctctcctt cgagctgctg 1260
catgcccctg ccacagtgtg cggacctaaa aagtccacca acctcgtgaa gaacaagaga 1320
gtgcagccta cagagagcat cgtgaggttc cccaacatca ccaacctgtg ccctttcggc 1380
gaggtgttta acgctacaag attcgctagc gtgtacgctt ggaacagaaa gagaatctcc 1440
aattgcgtgg ccgactacag cgtgctgtac aacagcgcta gcttcagcac cttcaagtgc 1500
tacggagtgt cccctaccaa gctgaacgac ctgtgcttca ccaacgtgta cgccgatagc 1560
ttcgtgatta gaggagacga agtgagacag attgctcctg gacagaccgg caacatcgcc 1620
gactacaatt acaagctgcc tgatgacttt accggctgtg tgattgcctg gaacagcaac 1680
aacctggaca gcaaggtggg cggcaactac aactatctgt acagactctt cagaaagagc 1740
aatctgaagc cttttgaaag ggacatcagc accgagatct atcaagccgg cagcacccct 1800
tgcaacggag tcaagggctt caactgctac tttcctctgc agagctatgg ctttcagcct 1860
acctacggcg tcggatatca gccttacaga gtcgtggtgc tgagcttcga gctgctccac 1920
gcccctgcca ccgtctgcgg ccctaagaaa agcaccaacc tggtcaagaa caaatga 1977

<210> SEQ ID NO 16
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 16
atgagggtgc agcccacaga gagcatcgtc agattcccta acatcacaaa cctgtgtcct 60
tttggcgagg tcttcaacgc cacaagattc gctagcgtgt acgcctggaa tagaaaaagg 120
attagcaact gtgtggctga ctacagcgtc ctgtataaca gcgcttcctt ttccaccttt 180
aagtgttatg gcgtgtcccc cacaaagctg aacgacctgt gttttaccaa tgtgtacgcc 240
gacagcttcg tcatcagagg agacgaggtg agacaaatcg cccctggaca gaccggcaac 300
atcgccgact acaattataa gctgcctgac gactttaccg gctgcgtgat tgcttggaac 360
tccaacaacc tggatagcaa ggtgggagga aactacaact acctctacag actcttcaga 420
aagagcaatc tgaagccttt cgagagagat atctccacag agatctatca agccggcagc 480
accccttgta acggagtgaa gggattcaat tgttatttcc ctctgcaaag ctatggattt 540
cagcctacct acggagtggg atatcagccc tatagagtgg tcgtgctgag cttcgagctc 600
ctgcacgccc ctgctacagt ctgtggccct aagaagtcca caaacctcgt gaagaacaag 660
agagtgcagc ctaccgagag catcgtgagg ttccctaaca ttaccaacct ctgtcctttt 720
ggagaagtct ttaatgccac aagatttgct agcgtgtacg cttggaatag aaagaggatt 780
tccaattgcg tggccgacta ctccgtcctg tacaacagcg ctagcttcag caccttcaaa 840
tgctacggag tgagccctac caagctcaac gacctgtgct ttaccaacgt gtacgctgac 900
agcttcgtca ttaggggaga cgaggtgagg cagatcgctc ctggacagac cggcaacatc 960
gccgactaca actacaagct gcccgacgat ttcaccggct gcgtcattgc ctggaatagc 1020
aacaatctgg acagcaaggt gggaggaaac tataattacc tgtacagact gtttaggaaa 1080
agcaacctca aacccttcga aagagacatt agcacagaga tctaccaagc cggctccacc 1140
ccctgcaatg gcgtgaaggg atttaattgt tacttccccc tgcagagcta tggctttcaa 1200
cctacctacg gcgtgggcta tcagccctat agggtggtgg tcctcagctt tgaactcctg 1260
cacgctcctg ccaccgtgtg cggccccaaa aagagcacca atctggtcaa gaacaagaga 1320
gtgcagccca cagagtccat cgtgagattt cctaatatta ccaacctgtg ccctttcgga 1380
gaggtgttta atgctacaag atttgctagc gtctatgcct ggaacagaaa gagaatcagc 1440
aactgcgtgg ccgattacag cgtcctgtac aatagcgctt ccttctccac ctttaaatgc 1500
tacggcgtga gccccaccaa gctgaatgac ctctgtttca ccaacgtgta tgccgactcc 1560
tttgtgatta gaggagatga ggtgagacag atcgcccctg gacaaaccgg caacattgcc 1620
gattacaatt acaagctgcc tgatgacttc accggctgtg tgattgcctg gaacagcaat 1680
aacctggaca gcaaggtggg cggcaattat aactacctgt atagactgtt cagaaagagc 1740
aacctgaagc cttttgagag agacatcagc accgagattt accaagccgg ctccacccct 1800
tgcaacggcg tgaagggctt caattgctac ttccctctgc agtcctacgg ctttcagcct 1860
acatacggcg tgggatatca gccttataga gtcgtggtgc tcagcttcga gctgctgcac 1920
gcccccgcta cagtgtgtgg acctaaaaag tccaccaatc tcgtcaagaa taagtga 1977

<210> SEQ ID NO 17
<211> LENGTH: 1977
<212> TYPE: DNA
<213> ORGANISM: Artificial Sequence
<220> FEATURE:
<223> OTHER INFORMATION: SARS-CoV-2

<400> SEQUENCE: 17
atgagagtgc agcctaccga gagcatcgtg agattcccta acatcaccaa cctctgccct 60
ttcggagagg tcttcaacgc cacaagattt gctagcgtgt acgcctggaa cagaaaaaga 120
atctccaact gcgtggccga ctacagcgtc ctgtacaata gcgctagctt cagcaccttc 180
aagtgctacg gcgtctcccc tacaaagctg aatgacctgt gcttcaccaa cgtgtatgcc 240
gacagcttcg tgattagagg cgatgaggtg aggcagatcg cccctggaca aaccggcaac 300
atcgccgatt ataactacaa gctgcctgac gacttcaccg gctgcgtgat cgcctggaac 360
agcaacaacc tggacagcaa ggtcggcggc aactacaact acctctacag actgttcaga 420
aagtccaacc tgaagccttt cgagagggac atcagcaccg agatttacca agccggcagc 480 acccccttgca acggcgtgaa gggatttaac tgctatttcc ctctgcagag ctacggcttc 540
caacctacct atggagtggg ctaccaaccc tacagagtgg tggtcctgag cttcgaactg 600
ctgcacgccc ctgccaccgt gtgtggccct aaaaagagca ccaatctcgt gaaaaacaag 660
agagtgcagc ctacagaaag cattgtgaga tttcctaata tcaccaacct gtgccctttc 720
ggcgaggtgt tcaacgctac aagattcgct agcgtgtacg cctggaatag aaagagaatc 780
agcaactgcg tggccgacta cagcgtgctg tacaacagcg cttcctttag caccttcaag 840
tgttacggcg tgagccccac caagctcaac gacctgtgct tcacaaacgt gtacgctgac 900
agcttcgtga tcagaggcga tgaggtgaga cagatcgccc ctggccaaac cggcaacatc 960

```
gccgattaca actataagct ccctgatgac ttcaccggct gcgtgatcgc ttggaacagc   1020

aacaacctgg acagcaaggt gggcggcaac tacaactacc tctatagact gttcagaaaa   1080

tccaacctga agcctttcga gagagacatc tccaccgaga tttatcaagc cggaagcacc   1140

ccctgcaatg gcgtgaaggg cttcaactgc tacttccctc tccaatccta cggcttccaa   1200

cctacctacg gagtgggcta tcagccctac agagtggtcg tgctgagctt cgagctcctg   1260

cacgcccctg ccaccgtgtg cggccctaaa aagagcacca acctggtcaa aaataagaga   1320

gtgcagccca ccgagagcat cgtgagattc cctaatatca ccaacctgtg ccccttttgga  1380

gaggtgttca acgccacaag attcgctagc gtgtacgcct ggaatagaaa gaggatcagc   1440

aactgcgtgg ccgactacag cgtgctctac aacagcgcct ccttcagcac ctttaagtgt   1500

tacggcgtct cccctaccaa gctgaacgat ctctgcttta ccaacgtgta cgccgacagc   1560

tttgtgatca gaggcgacga agtgaggcaa atcgctcctg gacagaccgg aaacatcgcc   1620

gactacaact acaagctgcc tgacgacttc accggctgcg tcatcgcctg gaatagcaac   1680

aacctggata gcaaagtcgg aggcaactac aactacctgt acagactctt cagaaagagc   1740

aacctcaaac ctttcgagag agacatcagc acagagatct accaagccgg cagcacccct   1800

tgcaacggag tcaagggctt caactgctac tttcctctgc agagctacgg ctttcagcct   1860

acctacggcg tcggctatca gccttacaga gtggtcgtgc tcagcttcga actcctgcac   1920

gcccccgcca ccgtgtgcgg acctaaaaag agcaccaatc tggtgaagaa caaatga      1977


<210> SEQ ID NO 18
<211> LENGTH: 658
<212> TYPE: PRT
<213> ORGANISM: Artificial Sequence
<220> FEATURE:
<223> OTHER INFORMATION: SARS-CoV-2

<400> SEQUENCE: 18

Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190
```

-continued

```
Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Lys Ile
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Glu Gly Phe Asn Cys Tyr Phe Pro Leu Gln Ser Tyr Gly Phe Gln
385                 390                 395                 400

Pro Thr Asn Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys Arg Val Gln Pro Thr Glu Ser Ile Val
        435                 440                 445

Arg Phe Pro Asn Ile Thr Asn Leu Cys Pro Phe Gly Glu Val Phe Asn
    450                 455                 460

Ala Thr Arg Phe Ala Ser Val Tyr Ala Trp Asn Arg Lys Arg Ile Ser
465                 470                 475                 480

Asn Cys Val Ala Asp Tyr Ser Val Leu Tyr Asn Ser Ala Ser Phe Ser
                485                 490                 495

Thr Phe Lys Cys Tyr Gly Val Ser Pro Thr Lys Leu Asn Asp Leu Cys
            500                 505                 510

Phe Thr Asn Val Tyr Ala Asp Ser Phe Val Ile Arg Gly Asp Glu Val
        515                 520                 525

Arg Gln Ile Ala Pro Gly Gln Thr Gly Lys Ile Ala Asp Tyr Asn Tyr
    530                 535                 540

Lys Leu Pro Asp Asp Phe Thr Gly Cys Val Ile Ala Trp Asn Ser Asn
545                 550                 555                 560

Asn Leu Asp Ser Lys Val Gly Gly Asn Tyr Asn Tyr Leu Tyr Arg Leu
                565                 570                 575

Phe Arg Lys Ser Asn Leu Lys Pro Phe Glu Arg Asp Ile Ser Thr Glu
            580                 585                 590

Ile Tyr Gln Ala Gly Ser Thr Pro Cys Asn Gly Val Glu Gly Phe Asn
        595                 600                 605
```

-continued

```
Cys Tyr Phe Pro Leu Gln Ser Tyr Gly Phe Gln Pro Thr Asn Gly Val
    610                 615                 620

Gly Tyr Gln Pro Tyr Arg Val Val Val Leu Ser Phe Glu Leu Leu His
625                 630                 635                 640

Ala Pro Ala Thr Val Cys Gly Pro Lys Lys Ser Thr Asn Leu Val Lys
                645                 650                 655

Asn Lys


<210> SEQ ID NO 19
<211> LENGTH: 439
<212> TYPE: PRT
<213> ORGANISM: Artificial Sequence
<220> FEATURE:
<223> OTHER INFORMATION: SARS-CoV-2

<400> SEQUENCE: 19

Met Arg Val Gln Pro Thr Glu Ser Ile Val Arg Phe Pro Asn Ile Thr
1               5                   10                  15

Asn Leu Cys Pro Phe Gly Glu Val Phe Asn Ala Thr Arg Phe Ala Ser
            20                  25                  30

Val Tyr Ala Trp Asn Arg Lys Arg Ile Ser Asn Cys Val Ala Asp Tyr
        35                  40                  45

Ser Val Leu Tyr Asn Ser Ala Ser Phe Ser Thr Phe Lys Cys Tyr Gly
    50                  55                  60

Val Ser Pro Thr Lys Leu Asn Asp Leu Cys Phe Thr Asn Val Tyr Ala
65                  70                  75                  80

Asp Ser Phe Val Ile Arg Gly Asp Glu Val Arg Gln Ile Ala Pro Gly
                85                  90                  95

Gln Thr Gly Lys Ile Ala Asp Tyr Asn Tyr Lys Leu Pro Asp Asp Phe
            100                 105                 110

Thr Gly Cys Val Ile Ala Trp Asn Ser Asn Asn Leu Asp Ser Lys Val
        115                 120                 125

Gly Gly Asn Tyr Asn Tyr Leu Tyr Arg Leu Phe Arg Lys Ser Asn Leu
    130                 135                 140

Lys Pro Phe Glu Arg Asp Ile Ser Thr Glu Ile Tyr Gln Ala Gly Ser
145                 150                 155                 160

Thr Pro Cys Asn Gly Val Glu Gly Phe Asn Cys Tyr Phe Pro Leu Gln
                165                 170                 175

Ser Tyr Gly Phe Gln Pro Thr Asn Gly Val Gly Tyr Gln Pro Tyr Arg
            180                 185                 190

Val Val Val Leu Ser Phe Glu Leu Leu His Ala Pro Ala Thr Val Cys
        195                 200                 205

Gly Pro Lys Lys Ser Thr Asn Leu Val Lys Asn Lys Arg Val Gln Pro
    210                 215                 220

Thr Glu Ser Ile Val Arg Phe Pro Asn Ile Thr Asn Leu Cys Pro Phe
225                 230                 235                 240

Gly Glu Val Phe Asn Ala Thr Arg Phe Ala Ser Val Tyr Ala Trp Asn
                245                 250                 255

Arg Lys Arg Ile Ser Asn Cys Val Ala Asp Tyr Ser Val Leu Tyr Asn
            260                 265                 270

Ser Ala Ser Phe Ser Thr Phe Lys Cys Tyr Gly Val Ser Pro Thr Lys
        275                 280                 285

Leu Asn Asp Leu Cys Phe Thr Asn Val Tyr Ala Asp Ser Phe Val Ile
    290                 295                 300

Arg Gly Asp Glu Val Arg Gln Ile Ala Pro Gly Gln Thr Gly Lys Ile
```

-continued

```
305                 310                 315                 320

Ala Asp Tyr Asn Tyr Lys Leu Pro Asp Asp Phe Thr Gly Cys Val Ile
                325                 330                 335

Ala Trp Asn Ser Asn Asn Leu Asp Ser Lys Val Gly Gly Asn Tyr Asn
            340                 345                 350

Tyr Leu Tyr Arg Leu Phe Arg Lys Ser Asn Leu Lys Pro Phe Glu Arg
        355                 360                 365

Asp Ile Ser Thr Glu Ile Tyr Gln Ala Gly Ser Thr Pro Cys Asn Gly
    370                 375                 380

Val Glu Gly Phe Asn Cys Tyr Phe Pro Leu Gln Ser Tyr Gly Phe Gln
385                 390                 395                 400

Pro Thr Asn Gly Val Gly Tyr Gln Pro Tyr Arg Val Val Val Leu Ser
                405                 410                 415

Phe Glu Leu Leu His Ala Pro Ala Thr Val Cys Gly Pro Lys Lys Ser
            420                 425                 430

Thr Asn Leu Val Lys Asn Lys
        435
```